US008030064B2

(12) United States Patent
Lee et al.

(10) Patent No.: US 8,030,064 B2
(45) Date of Patent: Oct. 4, 2011

(54) METHOD FOR WHOLE SURROUNDING SURFACE DISPLAY OF TARGET PROTEINS USING BACTERIAL EXOSPORIUM

(75) Inventors: Sang Yup Lee, Daejeon (KR); Tae Jung Park, Daejeon (KR); Jong Pil Park, Yongin (KR); Seok Jae Lee, Daejeon (KR); Jae-Gu Pan, Chungcheongnamdo (KR); Heung-Chae Jung, Deajeon (KR); Soo-Keun Choi, Deajeon (KR)

(73) Assignees: Korea Advanced Institute of Science and Technology, Daejeon (KR); Genofocus, Inc., Daejeon (KR)

( * ) Notice: Subject to any disclaimer, the term of this patent is extended or adjusted under 35 U.S.C. 154(b) by 826 days.

(21) Appl. No.: 10/572,224

(22) PCT Filed: Dec. 30, 2003

(86) PCT No.: PCT/KR03/02882

§ 371 (c)(1), (2), (4) Date: Apr. 18, 2007

(87) PCT Pub. No.: WO2005/028654

PCT Pub. Date: Mar. 31, 2005

(65) Prior Publication Data

US 2007/0269838 A1 Nov. 22, 2007

(30) Foreign Application Priority Data

Sep. 19, 2003 (KR) ........................ 10-2003-0064998

(51) Int. Cl.
*C12N 15/00* (2006.01)
*C12N 1/21* (2006.01)

(52) U.S. Cl. ................................ 435/320.1; 435/252.31

(58) Field of Classification Search ........................ None
See application file for complete search history.

(56) References Cited

U.S. PATENT DOCUMENTS

| | | | |
|---|---|---|---|
| 6,117,976 | A | 9/2000 | Neri et al. |
| 6,406,921 | B1 | 6/2002 | Wagner et al. |
| 2002/0055125 | A1 | 5/2002 | Charych et al. |
| 2002/0055186 | A1 | 5/2002 | Barry et al. |

FOREIGN PATENT DOCUMENTS

| | | | |
|---|---|---|---|
| KR | 1020020045400 | A | 6/2002 |
| WO | WO-01/83827 | A1 | 11/2001 |
| WO | 0246388 | A1 | 6/2002 |
| WO | WO-02/50260 | A3 | 6/2002 |
| WO | WO-0246388 | | 6/2002 |

OTHER PUBLICATIONS

Bailey-Smith et al., J. Bacteriol., 2005, vol. 187, No. 11, p. 3800-3806.*

Edlund, T., et al., Evidence for two immune inhibitors from *Bacillusthuringiensis* interfering with the humoral defense system of Saturniid.., Infect Immunol., Oct. 1976, pp. 934-941, vol. 14.

Georgiou, George, Analysis of large libraried of protein mutants using flow cytometry , Adv. Protein Chem., 2001, pp. 293-315, vol. 55.

Martineau, P., et al., A Genetic System to Elicit and Monitor Anti-Peptide Antibodies Without Peptide Synthesis, Bio/Technology, Feb. 1991, pp. 170-172, vol. 9, No. 2.

Miller, Jeffrey H., Experiments in Molecular Genetics, 1972, pp. 352-355, Publisher: Cold Spring Harbor Laboratory Press, Published in: Cold Spring Harbor, NY.

Nicholson, W.L., et al., Chapter 9: Sporulation, Germination and Outgrowth, Molecular Biological Methods for *Bacillus* (Harwood, C.R. and Cutting, S.M., Eds.), 1990, p. 416, Publisher: John Wiley & Sons., Ltd.

Agterberg, Marja, et al., Outer-membrane PhoE protein of *Escherichia coli* K-12 as an exposure vector: possibilities and limitations , Gene, Mar. 1990, pp. 37-45, vol. 88, No. 1.

Cadwell, R.C., et al., Randomization of genes by PCR mutagenesis., PCR Methods Appl., Aug. 1992, pp. 28-33, vol. 2, No. 1.

Charbit, A., et al., Presentation of two epitopes of the preS2 region of hepatitis B virus on live recombinant bacteria, Journal of Immunology, Sep. 1987, pp. 1658-1664, vol. 139, No. 5.

Desrosier, John P., Isolation and properties of pili from spores of *Bacillus cereus*, Journal of Bacteriology, Jan. 1981, pp. 613-619, vol. 145, No. 1.

(Continued)

*Primary Examiner* — Nancy Vogel

(74) *Attorney, Agent, or Firm* — Steven J. Hultquist; Kelly K. Reynolds; Hultquist IP

(57) ABSTRACT

The present invention relates to a method for expressing a target protein on an exosporium forming the outermost surface of bacterial spores. More particularly, the present invention relates to a method for expressing a target protein on the surface of cells and spores using an exosporium as a matrix for surface expression, and methods for the production of a protein array, the production of antibodies, the separation of a certain substance from a mixture, bioconversion, and the improvement of a target protein, which are characterized by using the cells or spores having the target protein that was expressed on the surface by the above expression method. The method for expressing the target protein on the surface of the spore outer membrane of the gene carriers according to the present invention has effects in that a variety of the target proteins can be expressed and the level of surface expression of the target protein is increased compared to the existing technology, and also the structural stability of the gene carriers having the target protein expressed on their surface, the viability of the host, and the rapidity of the screening method, are greatly increased.

2 Claims, 14 Drawing Sheets

OTHER PUBLICATIONS

Desrosier, J.P., et al., Synthesis of the exosporium during sporulation of *Bacillus cereus*, J. Gen. Microbiol., 1984, pp. 935-940, vol. 130, No. 4.

Freeman, Amihay, et al., Site-protected fixation and immobilization of *Escherichia coli* cells displaying surface-anchored beta-lactamase, Biotechnology and Bioengineering, Jan. 1999, pp. 155-159, vol. 62, No. 2.

Georgiou, George, et al., Practical applications of engineering Gram-negative bacterial cell surfaces, Trends in Biotechnology, Jan. 1993, pp. 6-10, vol. 11, No. 1.

Georgiou, George, et al., Display of β-lactamase on the *Escherichia coli* surface: outer membrane phenotypes conferred by Lpp'-OmpA'-β-lactamase fu, Protein Engineering, 1996, pp. 239-247, vol. 9, No. 2.

Georgiou, George, et al., Display of heterologous proteins on the surface of microorganisms: From the screening of combinatorial libraries to . . . , Nature Biotechnology, Jan. 1997, pp. 29-34, vol. 15, No. 1.

Harwood, Colin R., et al. (Ed.), Molecular Biological Methods for *Bacillus*, Nov. 1990, p. 416, Publisher: John Wiley & Sons, Ltd., Published in: New York.

Kalman, Sue, et al., Cloning of a novel crylC-type gene from a strain of *Bacillus thuringiensis* subsp. *galleriae*, Applied and Environmental Microbiology, Apr. 1993, pp. 1131-1137, vol. 59, No. 4.

Kawamura, F., et al., Construction of a *Bacillus subtilis* double mutant deficient in extracellular alkaline and neutral proteases, Journal of Bacteriology, Oct. 1984, pp. 442-444, vol. 160, No. 1.

Kim, Yong-Sung, et al., Bacterial Cell Surface Display of an Enzyme Library for Selective Screening of Improved Cellulase Variants , Applied and Environmental Microbiology, Feb. 2000, pp. 788-793, vol. 66, No. 2.

Lee, Sang Yup, et al., Microbial cell-surface display, Trends in Biotechnology, Jan. 2003, pp. 45-52, vol. 21, No. 1.

Lee, Jong Soo, et al., Surface-displayed viral antigens on *Salmonella* carrier vaccine, Nature Biotechnology, Jun. 2000, pp. 645-648, vol. 18, No. 6.

Lutz, Stefan, et al., Homology-independent protein engineering , Current Opinion in Biotechnology, Aug. 2000, pp. 319-324, vol. 11, No. 4.

Munakata, N., et al. Inactivation action spectra of *Bacillus subtilis* spores in extended ultraviolet wavelengths (50-300 nm) obtained with . . . , Photochemistry and Photobiology, Nov. 1991, pp. 761-768, vol. 54, No. 5.

Ness, Jon E., et al., DNA shuffling of subgenomic sequences of subtilisin, Nature Biotechnology, Sep. 1999, pp. 893-896, vol. 17, No. 9.

Perego, M., et al., Aspartyl-phosphate phosphatases deactivate the response regulator components of the sporulation signal transduction . . . , Molecular Microbiology, Mar. 1996, pp. 1151-1157, vol. 19, No. 6.

Popham, David L., et al., Spore Peptidoglycan Structure in a cwlD dacB Double Mutant of *Bacillus subtilis* , Journal or Bacteriology, Oct. 1999, pp. 6205-6209, vol. 181, No. 19.

Sambrook, Joseph, et al., Molecular Cloning, A Laboratory Manual, 1989, Publisher: Cold Spring Harbor Laboratory Press, Published in: Cold Spring Harbor, NY.

Samuelson, Patrik, et al., Staphylococcal Surface Display of Metal-Binding Polyhistidyl Peptides , Applied and Environmental Microbiology, Mar. 2000, pp. 1243-1248, vol. 66, No. 3.

Shao, Z., et al., Random-priming in vitro recombination: an effective tool for directed evolution, Nucleic Acids Research, Jan. 1998, pp. 681-683, vol. 26, No. 2.

Sousa, Carolina, et al., Enhanced metalloadsorption of bacterial cells displaying poly-His peptides, Nature Biotechnology, Aug. 1996, pp. 1017-1020, vol. 14, No. 8.

Steichen, Christopher, et al., Identification of the Immunodominant Protein and Other Proteins of the *Bacillus anthracis* Exosporium , Journal of Becteriology, Mar. 2003, pp. 1903-1910, vol. 185, No. 6.

Stemmer, Willem P.C., Rapid evolution of a protein in vitro by DNA shuffling, Nature, Aug. 1994, pp. 389-391, vol. 370.

Sylvestre, Patricia, et al., A collagen-like surface glycoprotein is a structural component of the *Bacillus anthracis* exosporium, Molecular Biology, Jul. 2002, pp. 169-178, vol. 45, No. 1.

Sylvestre, P., et al., Polymorphism in the collagen-like region of the *Bacillus anthracis* BclA protein leads to variation in exosporium filamen, Journal of Bacteriology, Mar. 2003, pp. 1555-1563, vol. 185, No. 5.

Tennen, R., et al., Mechanisms of killing of spores of *Bacillus subtilis* by iodine, glutaraldehyde and nitrous acid , Journal of Applied Microbiology, Aug. 2000, pp. 330-338, vol. 89, No. 2.

Todd, S.J., et al., Genes of *Bacillus cereus* and *Bacillus anthracis* encoding proteins of the exosporium, Journal of Bacteriology, Jun. 2003, pp. 3373-3378, vol. 185, No. 11.

Wiencek, K. Mark, et al., Hydrophobicity of *Bacillus* and *Clostridium* spores, Applied and Environmental Microbiology, Sep. 1990, pp. 2600-2605, vol. 56, No. 9.

Zhao, Huimin, et al., Molecular evolution by staggered extension process (StEP) in vitro recombination, Nature Biotechnology, Mar. 1998, pp. 258-261, vol. 16, No. 3.

* cited by examiner

SEQUENCE LISTING

```
<160> NUMBER OF SEQ ID NOS: 33

<210> SEQ ID NO 1
<211> LENGTH: 22
<212> TYPE: DNA
<213> ORGANISM: Artificial
```

<220> FEATURE:
<223> OTHER INFORMATION: PCR primer for repB cloning in bacillus
      subtilis 168 genomic DNA

<400> SEQUENCE: 1
ggaattcaaa gcacctgaaa ag 22

<210> SEQ ID NO 2
<211> LENGTH: 23
<212> TYPE: DNA
<213> ORGANISM: Artificial
<220> FEATURE:
<223> OTHER INFORMATION: PCR primer repB cloning in Bacillus subtilis
      168 genomic DNA

<400> SEQUENCE: 2
aactgcagct actctttaat aaa 23

<210> SEQ ID NO 3
<211> LENGTH: 86
<212> TYPE: DNA
<213> ORGANISM: Artificial
<220> FEATURE:
<223> OTHER INFORMATION: Artificial sequence for multicloning site in
      pSD1

<400> SEQUENCE: 3
catatggtcg acctgcaggc ggccgcgcta gcgaattcac tagtgatatc gaattcccgc 60
ggccgccatg gcggccggga gcatgc 86

<210> SEQ ID NO 4
<211> LENGTH: 2388
<212> TYPE: DNA
<213> ORGANISM: Bacillus thuringiensis

<400> SEQUENCE: 4
atgaacaaga aaccgttcaa agttttgtca tcaatcgctt taacagctgt attaggcctt 60
tcattcggag ctggcactca atctgcatat gctgaaacgc ctgtgaataa aacagctacg 120
agcccagttg atgatcattt aattccggaa gaacgtttag cagatgcgct aaaaaaacgt 180
ggggtaattg attcgaaggc ttcagagaca gaaacaaaga aagcagtcga aaagtatgta 240
gagaacaaaa agggtgaaaa ttctggaaaa gaagcagcaa atggggacca gcttacgaaa 300
gatgcatccg actttttaaa gaaagtaaaa gatgcgaaag cagacacgaa agaaaaatta 360
aatgaaccag caacagggac acctgcagcg acaggcccag ttaaaggcgg actaaatggt 420
aaagtgccaa cttctccagc aaaacaaaaa gactataacg gtgaagttcg taaagacaaa 480
gtactcgttt tacttgtaga gtacgctgac tttaaacata ataatatcga caaagagcct 540
ggatatatgt attctaacga ttttaataaa gaacattatg aaaaaatgtt attcggcaac 600
gagccattca cattagatga tggaagcaaa atcgaaacat ttaaacaata ttacgaagag 660
caatctggtg gtagttacac agtggacgga acagttacaa aatggttaac agtttctggt 720
aaagctgctg attacggtgc agatgctgct acaggtcatg ataataaagg accaaaaggg 780
ccacgtgatt tagtaaaaga tgcattaaaa gcagctgtag atagtggtat tgatttatca 840
gagtttgatc aatttgatca atacgatgta aatggtgatg gaaataaaaa tcaaccagat 900
ggtttaatcg atcaattaat gattattcat gcgggtgttg gacaagaagc aggcggtggt 960
aaattaggcg atgatgcaat ttggtcgcac cgttggacag ttggaccaaa gccattccca 1020
attgaaggta cacaagcgaa agttccatat tggggcggaa agatggcagc atttgactac 1080

-continued

```
acaattgaac cagaagatgg agcggttggt gtattcgcac atgaatatgg tcacgattta   1140

ggtcttccag atgagtacga tacacaatat agtggtcaag gtgagccgat tgaagcttgg   1200

tctattatga gtggcggaag ctgggctggt aaaatcgctg gaacgacgcc aacgagtttc   1260

tcaccacaaa ataaagagtt tttccaaaaa acaattggtg gtaactgggc aaatatcgta   1320

gaagtagatt acgagaaatt aaataaaggt atcggtctag cgacatattt ggatcaaagt   1380

gttacgaaat cagatcgacc aggtatgatt cgtgttaact taccagataa agatgttaaa   1440

acaattgagc cagcatttgg taaacaatat tattacagca caaaaggtga cgatcttcat   1500

acgaagatgg aaacaccgtt gtttgattta acgaatgcaa cgaatgcaaa atttgatttc   1560

aagtcattat atgagattga agcaggttat gatttccttg aagtacacgc tgtaacagaa   1620

gatggtaaac aaacgttaat tgaaagactt ggcgagaaag caactagtgg aaatgcagat   1680

tcgacaaatg gaaaatggat tgacaaatca tatgatttaa gtcaattcaa aggcaagaaa   1740

gtaaaattaa catttgatta cattactgat ggtggtttag cattaaatgg attcgctctt   1800

gataatgctt cattaacagt agatggtaaa gtagtattct ctgatgatgc agaaggtaca   1860

ccacaattaa aattagatgg tttcgttgta tctaacggaa cagaaaagaa aaaacataac   1920

tactatgttg agtggagaaa ctatgctggg gcagataacg cgttgaaatt tgctcgcggt   1980

ccagtattta acactggtat ggttgtatgg tatgcagatt cagcttatac agataactgg   2040

gttggtgtac atccaggaca cggtttcctt ggtgttgttg attctcatcc agaagcaatt   2100

gttggtactt taaatggtaa accaacagtt aagagcagta cacgattcca aatcgctgat   2160

gctgcgttct cattcgacaa aacgccagct tggaaagttg tatctccaac gcgtggaaca   2220

tttacgtatg atggcttagc aggcgtaccg aagtttgatg attcgaaaac gtatattaat   2280

caacagattc cagatgcagg acgtatttta ccgaagcttg gtttaaaatt tgaagtagta   2340

ggacaagctg atgataattc tgcaggtgct gttcgtttat atcgttaa                 2388
```

<210> SEQ ID NO 5
<211> LENGTH: 39
<212> TYPE: DNA
<213> ORGANISM: Artificial
<220> FEATURE:
<223> OTHER INFORMATION: PCR primer IAP1

<400> SEQUENCE: 5

```
cttatcttta ctagtatgta attcctccct aattatcgg                            39
```

<210> SEQ ID NO 6
<211> LENGTH: 32
<212> TYPE: DNA
<213> ORGANISM: Artificial
<220> FEATURE:
<223> OTHER INFORMATION: PCR primer for IAP2

<400> SEQUENCE: 6

```
ccgagctcgt cgacatgtaa ttcctcccta at                                   32
```

<210> SEQ ID NO 7
<211> LENGTH: 27
<212> TYPE: DNA
<213> ORGANISM: Artificial
<220> FEATURE:
<223> OTHER INFORMATION: PCR primer INCM-1

<400> SEQUENCE: 7

```
ctagctagcg cagggacaaa aacgcca                                         27
```

-continued

<210> SEQ ID NO 8
<211> LENGTH: 26
<212> TYPE: DNA
<213> ORGANISM: Artificial
<220> FEATURE:
<223> OTHER INFORMATION: PCR primer INCM-2

<400> SEQUENCE: 8
ggggtaccct aatttggttc tgttcc 26

<210> SEQ ID NO 9
<211> LENGTH: 27
<212> TYPE: DNA
<213> ORGANISM: Artificial
<220> FEATURE:
<223> OTHER INFORMATION: PCR primer INLZ-1

<400> SEQUENCE: 9
atagctagcc acggttacga tgcgccc 27

<210> SEQ ID NO 10
<211> LENGTH: 26
<212> TYPE: DNA
<213> ORGANISM: Artificial
<220> FEATURE:
<223> OTHER INFORMATION: PCR primer INLZ-2

<400> SEQUENCE: 10
ggggtacctt atttttgaca ccagac 26

<210> SEQ ID NO 11
<211> LENGTH: 672
<212> TYPE: DNA
<213> ORGANISM: Bacillus anthracis

<400> SEQUENCE: 11
atgtcaaata ataattattc aaatggatta aaccccgatg aatctttatc agctagtgca 60
tttgacccta atcttgtagg acctacatta ccaccgatac caccatttac ccttcctacc 120
ggaccaactg ggccaactgg accaactggg ccaactgggc caactggaga cactggtact 180
actggaccaa ctgggccaac tggaccaact gggccaactg gtgctaccgg actgactgga 240
ccgactggac cgactgggcc atccggacta ggacttccag caggactata tgcatttaac 300
tccggtggga tttctttaga tttaggaatt aatgatccag taccatttaa tactgttgga 360
tctcagtttg gtacagcaat ttctcaatta gatgctgata ctttcgtaat tagtgaaact 420
ggattctata aaattactgt tatcgctaat actgcaacag caagtgtatt aggaggtctt 480
acaatccaag tgaatggagt acctgtacca ggtactggat caagtttgat ttcactcgga 540
gcacctatcg ttattcaagc aattacgcaa attacgacaa ctccatcatt agttgaagta 600
attgttacag ggcttggact atcactagct cttggcacga gtgcatccat tattattgaa 660
aaagttgctt aa 672

<210> SEQ ID NO 12
<211> LENGTH: 735
<212> TYPE: DNA
<213> ORGANISM: Bacillus anthracis

<400> SEQUENCE: 12
atgtcaaata ataattattc aaatggatta aaccccgatg aatctttatc agctagtgca 60
tttgacccta atcttgtagg acctacatta ccaccgatac caccatttac ccttcctacc 120

-continued

```
ggaccaactg ggccgactgg accgactggg ccgactgggc caactggacc aactggacca    180

actgggccaa ctggaccaac tgggccaact gggccaactg gagacactgg tactactgga    240

ccaactgggc caactggacc aactggacca actgggccaa ctggtgctac cggactgact    300

ggaccgactg gaccgactgg gccatccgga ctaggacttc cagcaggact atatgcattt    360

aactccggtg ggatttcttt agatttagga attaatgatc cagtaccatt taatactgtt    420

ggatctcagt ttggtacagc aatttctcaa ttagatgctg atactttcgt aattagtgaa    480

actggattct ataaaattac tgttatcgct aatactgcaa cagcaagtgt attaggaggt    540

cttacaatcc aagtgaatgg agtacctgta ccaggtactg gatcaagttt gatttcactc    600

ggagcaccta tcgttattca agcaattacg caaattacga caactccatc attagttgaa    660

gtaattgtta cagggcttgg actatcacta gctcttggca cgagtgcatc cattattatt    720

gaaaaagttg cttaa                                                     735
```

<210> SEQ ID NO 13
<211> LENGTH: 762
<212> TYPE: DNA
<213> ORGANISM: Bacillus anthracis

<400> SEQUENCE: 13

```
atgtcaaata ataattattc aaatggatta aaccccgatg aatctttatc agctagtgca     60

tttgacccta atcttgtagg acctacatta ccaccgatac caccatttac ccttcctacc    120

ggaccaactg ggccgactgg accgactggg ccgactgggc caactggacc aactgggccg    180

actgggccaa ctggaccaac tggaccaact gggccaactg gaccaactgg gccaactggg    240

ccaactggag acactggtac tactggacca actgggccaa ctggaccaac tggaccaact    300

gggccaactg gtgctaccgg actgactgga ccgactggac cgactgggcc atccggacta    360

ggacttccag caggactata tgcatttaac tccggtggga tttctttaga tttaggaatt    420

aatgatccag taccatttaa tactgttgga tctcagtttg gtacagcaat ttctcaatta    480

gatgctgata ctttcgtaat tagtgaaact ggattctata aaattactgt tatcgctaat    540

actgcaacag caagtgtatt aggaggtctt acaatccaag tgaatggagt acctgtacca    600

ggtactggat caagtttgat ttcactcgga gcacctatcg ttattcaagc aattacgcaa    660

attacgacaa ctccatcatt agttgaagta attgttacag ggcttggact atcactagct    720

cttggcacga gtgcatccat tattattgaa aaagttgctt aa                       762
```

<210> SEQ ID NO 14
<211> LENGTH: 762
<212> TYPE: DNA
<213> ORGANISM: Bacillus anthracis

<400> SEQUENCE: 14

```
atgtcaaata ataattattc aaatggatta aaccccgatg aatctttatc agctagtgca     60

tttgacccta atcttgtagg acctacatta ccaccgatac caccatttac ccttcctacc    120

ggaccaactg ggccgactgg accgactggg ccgactgggc caactggacc aactgggccg    180

actgggccaa ctggaccaac tggaccaact gggccaactg gaccaactgg gccaactggg    240

ccaactggag acactggtac tactggacca actgggccaa ctggaccaac tggaccaact    300

gggccaactg gtgctaccgg actgactgga ccgactggac cgactgggcc atccggacta    360

ggacttccag caggactata tgcatttaac tccggtggga tttctttaga tttaggaatt    420

aatgatccag taccatttaa tactgttgga tctcagtttg gtacagcaat ttctcaatta    480
```

-continued

```
gatgctgata ctttcgtaat tagtgaaact ggattctata aaattactgt tatcgctaat    540

actgcaacag caagtgtatt aggaggtctt acaatccaag tgaatggagt acctgtacca    600

ggtactggat caagtttgat ttcactcgga gcacctatcg ttattcaagc aattacgcaa    660

attacgacaa ctccatcatt agttgaagta attgttacag ggcttggact atcactagct    720

cttggcacga gtgcatccat tattattgaa aaagttgctt aa                       762
```

<210> SEQ ID NO 15
<211> LENGTH: 762
<212> TYPE: DNA
<213> ORGANISM: Bacillus anthracis

<400> SEQUENCE: 15

```
atgtcaaata ataattattc aaatggatta aaccccgatg aatctttatc agctagtgca     60

tttgacccta atcttgtagg acctacatta ccaccgatac caccatttac ccttcctacc    120

ggaccaactg ggccgactgg accgactggg ccgactgggc caactggacc aactgggccg    180

actgggccaa ctggaccaac tggaccaact gggccaactg gagacactgg tactactgga    240

ccaactgggc caactggacc aactggacca actgggccaa ctggaccaac tggaccaact    300

gggccaactg gtgctaccgg actgactgga ccgactggac cgactgggcc atccggacta    360

ggacttccag caggactata tgcatttaac tccggtggga tttctttaga tttaggaatt    420

aatgatccag taccatttaa tactgttgga tctcagtttg gtacagcaat ttctcaatta    480

gatgctgata ctttcgtaat tagtgaaact ggattctata aaattactgt tatcgctaat    540

actgcaacag caagtgtatt aggaggtctt acaatccaag tgaatggagt acctgtacca    600

ggtactggat caagtttgat ttcactcgga gcacctatcg ttattcaagc aattacgcaa    660

attacgacaa cttcctcatt agttgaagta attgttacag ggcttggact atcactagct    720

cttggcacga gtgcatccat tattattgaa aaagttgctt aa                       762
```

<210> SEQ ID NO 16
<211> LENGTH: 789
<212> TYPE: DNA
<213> ORGANISM: Bacillus anthracis

<400> SEQUENCE: 16

```
atgtcaaata ataattattc aaatggatta aaccccgatg aatctttatc agctagtgca     60

tttgacccta atcttgtagg acctacatta ccaccgatac caccatttac ccttcctacc    120

ggaccaactg ggccgactgg accgactggg ccgactgggc caactggacc aactgggccg    180

actgggccaa ctggaccaac tgggccaact ggagacactg gtactactgg accaactggg    240

ccaactggac caactgggcc aactgggcca actggagaca ctggtactac tggaccaact    300

gggccaactg gaccaactgg accaactggg ccaactggtg ctaccggact gactggaccg    360

actggaccga ctgggccatc cggactagga cttccagcag gactatatgc atttaactcc    420

ggtgggattt ctttagattt aggaattaat gatccagtac catttaatac tgttggatct    480

cagtttggta cagcaatttc tcaattagat gctgatactt tcgtaattag tgaaactgga    540

ttctataaaa ttactgttat cgctaatact gcaacagcaa gtgtattagg aggtcttaca    600

atccaagtga atggagtacc tgtaccaggt actggatcaa gtttgatttc actcggagca    660

cctatcgtta ttcaagcaat tacgcaaatt acgacaactc catcattagt tgaagtaatt    720

gttacagggc ttggactatc actagctctt ggcacgagtg catccattat tattgaaaaa    780

gttgcttaa                                                            789
```

-continued

<210> SEQ ID NO 17
<211> LENGTH: 789
<212> TYPE: DNA
<213> ORGANISM: Bacillus anthracis

<400> SEQUENCE: 17
atgtcaaata ataattattc aaatggatta aaccccgatg aatctttatc agctagtgca 60
tttgacccta atcttgtagg acctacatta ccaccgatac caccatttac ccttcctacc 120
ggaccaactg ggccgactgg accgactggg ccgactgggc caactggacc aactgggccg 180
actgggccaa ctggaccaac tgggccaact ggagacactg gtactactgg accaactggg 240
ccaactggac caactgggcc aactgggcca actggagaca ctggtactac tggaccaact 300
gggccaactg gaccaactgg accaactggg ccaactggtg ctaccggact gactggaccg 360
actggaccga ctgggccatc cggactagga cttccagcag gactatatgc atttaactcc 420
ggtgggattt ctttagattt aggaattaat gatccagtac catttaatac tgttggatct 480
cagtttggta cagcaatttc tcaattagat gctgatactt tcgtaattag tgaaactgga 540
ttctataaaa ttactgttat cgctaatact gcaacagcaa gtgtattagg aggtcttaca 600
atccaagtga atggagtacc tgtaccaggt actggatcaa gtttgatttc actcggagca 660
cctatcgtta ttcaagcaat tacgcaaatt acgacaactc catcattagt tgaagtaatt 720
gttacagggc ttggactatc actagctctt ggcacgagtg catccattat tattgaaaaa 780
gttgcttaa 789

<210> SEQ ID NO 18
<211> LENGTH: 789
<212> TYPE: DNA
<213> ORGANISM: Bacillus anthracis

<400> SEQUENCE: 18
atgtcaaata ataattattc aaatggatta aaccccgatg aatctttatc agctagtgca 60
tttgacccta atcttgtagg acctacatta ccaccgatac caccatttac ccttcctacc 120
ggaccaactg ggccgactgg accgactggg ccgactgggc caactggacc aactgggccg 180
actgggccaa ctggaccaac tgggccaact ggagacactg gtactactgg accaactggg 240
ccaactggac caactgggcc aactgggcca actggagaca ctggtactac tggaccaact 300
gggccaactg gaccaactgg accaactggg ccaactggtg ctaccggact gactggaccg 360
actggaccga ctgggccatc cggactagga cttccagcag gactatatgc atttaactcc 420
ggtgggattt ctttagattt aggaattaat gatccagtac catttaatac tgttggatct 480
cagtttggta cagcaatttc tcaattagat gctgatactt tcgtaattag tgaaactgga 540
ttctataaaa ttactgttat cgctaatact gcaacagcaa gtgtattagg aggtcttaca 600
atccaagtga atggagtacc tgtaccaggt actggatcaa gtttgatttc actcggagca 660
cctatcgtta ttcaagcaat tacgcaaatt acgacaactc catcattagt tgaagtaatt 720
gttacagggc ttggactatc actagctctt ggcacgagtg catccattat tattgaaaaa 780
gttgcttaa 789

<210> SEQ ID NO 19
<211> LENGTH: 1113
<212> TYPE: DNA
<213> ORGANISM: Bacillus anthracis

<400> SEQUENCE: 19

-continued atgtcaaata ataattattc aaatggatta aaccccgatg aatctttatc agctagtgca 60
tttgacccta atcttgtagg acctacatta ccaccgatac caccatttac ccttcctacc 120
ggaccaactg ggccgactgg accgactggg ccgactgggc caactggacc aactgggccg 180
actgggccaa ctggaccaac tgggccaact ggagacactg gtactactgg accaactggg 240
ccaactggac caactgggcc gactgggcca actggaccaa ctgggccgac tgggccaact 300
ggaccaactg ggccaactgg agacactggt actactggac caactgggcc aactggacca 360
actggaccaa ctgggccaac tggagacact ggtactactg gaccaactgg gccaactgga 420
ccaactggac caactgggcc gactggaccg actgggccga ctgggccaac tggaccaact 480
gggccgactg ggccaactgg accaactggg ccaactggag acactggtac tactggacca 540
actgggccaa ctggaccaac tggaccaact gggccaactg gagacactgg tactactgga 600
ccaactgggc caactggacc aactggacca actgggccaa ctggaccaac tgggccaact 660
ggtgctaccg gactgactgg accgactgga ccgactgggc catccggact aggacttcca 720
gcaggactat atgcatttaa ctccggtggg atttctttag atttaggaat taatgatcca 780
gtaccattta atactgttgg atctcagttt ggtacagcaa tttctcaatt agatgctgat 840
actttcgtaa ttagtgaaac tggattctat aaaattactg ttatcgctaa tactgcaaca 900
gcaagtgtat taggaggtct tacaatccaa gtgaatggag tacctgtacc aggtactgga 960
tcaagtttga tttcactcgg agcacctatc gttattcaag caattacgca aattacgaca 1020
actccatcat tagttgaagt aattgttaca gggcttggac tatcactagc tcttggcacg 1080
agtgcatcca ttattattga aaaagttgct taa 1113

<210> SEQ ID NO 20
<211> LENGTH: 1176
<212> TYPE: DNA
<213> ORGANISM: Bacillus anthracis

<400> SEQUENCE: 20
atgtcaaata ataattattc aaatggatta aaccccgatg aatctttatc agctagtgca 60
tttgacccta atcttgtagg acctacatta ccaccgatac caccatttac ccttcctacc 120
ggaccaactg ggccgactgg accgactggg ccgactgggc caactggacc aactgggccg 180
actgggccaa ctggaccaac tgggccaact ggagacactg gtactactgg accaactggg 240
ccgactgggc caactggacc aactgggcca actggagaca ctggtactac tggaccaact 300
gggccaactg gaccaactgg gccgactggg ccaactggac caactgggcc gactgggcca 360
actggaccaa ctgggccaac tggagacact ggtactactg gaccaactgg gccaactgga 420
ccaactggac caactgggcc aactggagac actggtacta ctggaccaac tgggccaact 480
ggaccaactg gaccaactgg gccgactgga ccgactgggc cgactgggcc aactggacca 540
actgggccga ctgggccaac tggaccaact gggccaactg gagacactgg tactactgga 600
ccaactgggc caactggacc aactggacca actgggccaa ctggagacac tggtactact 660
ggaccaactg ggccaactgg accaactgga ccaactgggc caactggacc aactgggcca 720
actggtgcta ccggactgac tggaccgact ggaccgactg ggccatccgg actaggactt 780
ccagcaggac tatatgcatt taactccggt gggatttctt tagatttagg aattaatgat 840
ccagtaccat ttaatactgt tggatctcag tttggtacag caatttctca attagatgct 900
gatactttcg taattagtga aactggattc tataaaatta ctgttatcgc taatactgca 960
acagcaagtg tattaggagg tcttacaatc caagtgaatg gagtacctgt accaggtact 1020

```
ggatcaagtt tgatttcact cggagcacct atcgttattc aagcaattac gcaaattacg   1080

acaactccat cattagttga agtaattgtt acagggcttg gactatcact agctcttggc   1140

acgagtgcat ccattattat tgaaaaagtt gcttaa                             1176
```

<210> SEQ ID NO 21
<211> LENGTH: 1338
<212> TYPE: DNA
<213> ORGANISM: Bacillus anthracis

<400> SEQUENCE: 21

```
atgtcaaata ataattattc aaatggatta aaccccgatg aatctttatc agctagtgca     60

tttgacccta atcttgtagg acctacatta ccaccgatac caccatttac ccttcctacc    120

ggaccaactg ggccgactgg accgactggg ccgactgggc caactggacc aactgggccg    180

actgggccaa ctggaccaac tgggccgact gggccaactg gaccaactgg gccaactgga    240

gacactggta ctactggacc aactgggccg actgggccaa ctggaccaac tgggccaact    300

ggagacactg gtactactgg accaactggg ccaactggac caactgggcc gactgggcca    360

actggaccaa ctgggccgac tgggccaact ggaccaactg ggccaactgg agacactggt    420

actactggac caactgggcc aactggacca actggaccaa ctgggccaac tggagacact    480

ggtactactg gaccaactgg gccaactgga ccaactggac caactgggcc gactggaccg    540

actgggccga ctgggccaac tggaccaact gggccgactg ggccaactgg accaactggg    600

ccaactggag acactggtac tactggacca actgggccaa ctggaccaac tggaccaact    660

gggccaactg gagacactgg tactactgga ccaactgggc caactggacc aactggacca    720

actgggccaa ctggagacac tggtactact ggaccaactg ggccaactgg accaactgga    780

ccaactgggc caactggaga cactggtact actggaccaa ctgggccaac tggaccaact    840

ggaccaactg ggccaactgg accaactgga ccaactgggc caactggtgc taccggactg    900

actggaccga ctggaccgac tgggccatcc ggactaggac ttccagcagg actatatgca    960

tttaactccg gtgggatttc tttagattta ggaattaatg atccagtacc atttaatact   1020

gttggatctc agtttggtac agcaatttct caattagatg ctgatacttt cgtaattagt   1080

gaaactggat tctataaaat tactgttatc gctaatactg caacagcaag tgtattagga   1140

ggtcttacaa tccaagtgaa tggagtacct gtaccaggta ctggatcaag tttgatttca   1200

ctcggagcac ctatcgttat tcaagcaatt acgcaaatta cgacaactcc atcattagtt   1260

gaagtaattg ttacagggct tggactatca ctagctcttg gcacgagtgc atccattatt   1320

attgaaaaag ttgcttaa                                                 1338
```

<210> SEQ ID NO 22
<211> LENGTH: 1149
<212> TYPE: DNA
<213> ORGANISM: Bacillus anthracis

<400> SEQUENCE: 22

```
atgtcaaata ataattattc aaatggatta aaccccgatg aatctttatc agctagtgca     60

tttgacccta atcttgtagg acctacatta ccaccgatac caccatttac ccttcctacc    120

ggaccaactg ggccgactgg accgactggg ccgactgggc caactggacc aactgggccg    180

actgggccaa ctggaccaac tgggccaact ggagacactg gtactactgg accaactggg    240

ccgactgggc caactggacc aactgggcca actggagaca ctggtactac tggaccaact    300

gggccaactg gaccaactgg gccgactggg ccaactggac caactgggcc aactggagac    360
```

-continued actggtacta ctggaccaac tgggccaact ggaccaactg gaccaactgg gccaactgga 420
gacactggta ctactggacc aactgggcca actggaccaa ctggaccaac tgggccgact 480
ggaccgactg ggccgactgg gccaactgga ccaactgggc cgactgggcc aactggacca 540
actgggccaa ctggagacac tggtactact ggaccaactg ggccaactgg accaactgga 600
ccaactgggc caactggaga cactggtact actggaccaa ctgggccaac tggaccaact 660
ggaccaactg ggccaactgg accaactggg ccaactggtg ctaccggact gactggaccg 720
actggaccga ctgggccatc cggactagga cttccagcag gactatatgc atttaactcc 780
ggtgggattt ctttagattt aggaattaat gatccagtac catttaatac tgttggatct 840
cagtttggta cagcaatttc tcaattagat gctgatactt tcgtaattag tgaaactgga 900
ttctataaaa ttactgttat cgctaatact gcaacagcaa gtgtattagg aggtcttaca 960
atccaagtga atggagtacc tgtaccaggt actggatcaa gtttgatttc actcggagca 1020
cctatcgtta ttcaagcaat tacgcaaatt acgacaactc catcattagt tgaagtaatt 1080
gttacagggc ttggactatc actagctctt ggcacgagtg catccattat tattgaaaaa 1140
gttgcttaa 1149

<210> SEQ ID NO 23
<211> LENGTH: 859
<212> TYPE: DNA
<213> ORGANISM: Bacillus cereus

<400> SEQUENCE: 23
attccactaa gtacattgga tgaacaaaaa aatcatatga aggcagcatg ttttctcatc 60
ccttctcagt tctcttcctt caatgtatgc gccttttctt gtccatacat ccgcaatcat 120
ctatttatat aaaattacac tcttgtcctg ttcagaaaga tgcctacata catatcatgt 180
taaggaaaaa gaatacettt tcactttaat acatgataag gaggatttct atgaaacgtg 240
atattagaaa agctgtcgaa gaaatcaaaa gtgctgggat ggaggatttc ttacaccaag 300
atccaagtac ttttgaatgc gatgatgata aattcactca tcatcattgt acaactggat 360
gtaaatgtac aactgggggt aaatgtccaa gaacaagatg tactcgcgtg aaacattgta 420
cgttcgttac aaaatgtacg catgtgaaaa aatggacatt tgttacgaaa tgtactcgtg 480
tacgtgttca aaaatggacg ttcgttacga aagtaacgcg tagaaaagaa tgcgtattag 540
ttacgaaacg tactcgcaga aaacattgta cattcattac aaaatgcata cgctttgaaa 600
agaaattttt ctggacaaaa cgaagtttct gtaaaaaatg cgaattcttc cctaacagac 660
acggtggctc ttgcgatgat tcatgtgatc atggtaaaga ctgtcacgat agcggacaca 720
aatggaatga ttgcaaaggc ggacataaat tcccatcttg caaaaataag aaattcgatc 780
acttctggta taaaaaacgt aactgctagt ttttatacca ccaaaaaaag gccgttttgc 840
ggcctttttt acatttatt 859

<210> SEQ ID NO 24
<211> LENGTH: 677
<212> TYPE: DNA
<213> ORGANISM: Bacillus cereus

<400> SEQUENCE: 24
aagaacgtat aactacgcct cgcttttctc aagtacaaaa ttaaatatta gattcactta 60
gcaacattta cgctcttgtc caatagctaa agcgctaaaa gatagtgggc caacaacttc 120
tgcgcttgca ccactagtaa ggttttctac agttaatgaa tattcgtgtg ttccactgct 180

```
aacgttttga tctatagctt gaaatgtttg tacatagaat tgttcagaat ctgtagattc    240

aatacctact tgtgcattaa aaatttcaat attatcacgg aaaattcgga ataaaacttg    300

tgaagtctca gttatacctt ctataccaat tgtagcgatt aattctactc gattattacg    360

tgaatctcta cttgaaattc gcaatttcaa atttgctaaa attgctttat ttggagaaga    420

tgggattgca aaagttgttt caccagtttt actaataggt tgagtagctt ggtaatcaat    480

gatatgagtc atattcttca cctcctcata tactagaata tgaaaatagt gaataattag    540

tttggacaaa tactagatta tttaatagag tcaacaataa ttattgaaaa gaagaaattc    600

acataaaagc attaagaata tatcacaata agatgatatt tttcttaatg ctttttgtaa    660

ttaagcagaa tattctt                                                   677
```

<210> SEQ ID NO 25
<211> LENGTH: 1075
<212> TYPE: DNA
<213> ORGANISM: Bacillus cereus

<400> SEQUENCE: 25

```
ttctttttca atattatttt ttatccgcga gcgtcttgaa tggcgctcct taatttttaa     60

ataacatttc caggtaatta cgagagcgga ttttattatg ttgtacaagc actaattcgc    120

tttattaaat agactatata gatatctaaa agaagggagc tttaaattca tatggctgat    180

tacttttata aagatggtaa aaaatattat aaaaaccaat cgcattcgaa cgaccaaaaa    240

aacaactgtt ttattgaaac tcatacgata gctggttctg cagaaaatga aaatggaaat    300

atacctgtat ctgttttcct tgaaaccacc gctccacaaa ctgtatttga ggattttaca    360

aacaatcata ataaaacatt aattcagtta ttcgttgtcg gtatgagtgc acctgttcaa    420

gtaactattc taacaagaag atctagcgta ccaattacta ctacattaca acctgttcaa    480

acaaaaatat ttcaagttga agattttcaa agtcttactc ttacaaagca ggaaggttct    540

actagtgtag ttagtttatt tgttcaaaaa acattttgta tatgctgtaa agataataac    600

gattcatgtg atgaatatta ccacgaatgt aattgatata ttaaatcacc agaagaaccc    660

tttatataaa gggttctttt cctttcactc ccctcatttt tctgtttttt attaaaataa    720

ctattttgtt aaaaatcttt cttcattctt tttagatcat gtaacatatc ttactaaata    780

aggatatatt ccacaaaatt ttgaaaggag gaatttttat taacacaact ttaatttctc    840

atttttataa cgaagagtat ctgcttccgt ggtggttaat gcaccacaca aaattatttg    900

atcatggcat tcttattaat cgtgggtcta ctgatcgttc ggttgaatta tgcaaattat    960

ttgcacctca ttgggaaatc cgtgaatcaa aggtattaga gtttgatgcc attttagttg   1020

atcaagaagt aatgaacata gaaaaagaaa ttacgggatg gaaaatggtg ctaaa        1075
```

<210> SEQ ID NO 26
<211> LENGTH: 1183
<212> TYPE: DNA
<213> ORGANISM: Bacillus cereus

<400> SEQUENCE: 26

```
gattggattg gtgttagaag gaattaaagc gattatatga gaaaaacctt ccgcaattgc     60

ggaaggtttt ttatttttcg agaacactca tattcaaatt ataagctttc tcaatattta    120

acttgtacgt cccatttcca gttttaatcg aatttttata ccaatgttct tgggtgttta    180

attctggatg ttcttctgaa gaagtatttt cgtttttcgt taaatcttct acttgttccc    240

aaggtgtact tccatgtgtt tctttttgat tcgttactgc tgttaaagaa acatcactct    300
```

-continued

```
cttttgcaag atggacagac actcttgagc tttcctgtac aaaccaatta ttttgcaatt    360

gacctggata aagagatagt tcgttatttg aagcacggat ttccacattt ttattttgtg    420

gaagaacaag cgttggtttc acctgtggtg ctgaattaaa taacgtatgc tgaacaggta    480

atgattttaa agtgatatac atcgtttctc cagccgtttg aactgaaagg aaatcatctc    540

gttttaaatt gagtttttca tttgctttcg ttgtcatttc ataagttccc aaaagatgaa    600

tttgatttgt attatttccc tctatcgtta gaggctgatg tcctgcatct actacgattt    660

ttttgataga ttcaggtata tcaaattgtc cgtctggaat attactcgtt tgcctcgttg    720

tattaataga atgacgaact tcttctagta atccagttga taataaacag taaaaagcaa    780

ttccgacact tcctaaaacg ccgataaaga aaatactaaa aatatcatat ttaataaaag    840

attgctcttt tttagagaat agaaggtata gtaaaacttc agctccaagt atgataagta    900

aaactggcca ccatgcagtt agtgtatcta atacttgaat tccttttacg actgaaaaaa    960

gtaaaaagca tcctaacgat ataatagaaa gccccattga gaatgttcca acacgccatg   1020

ttctcattct tttgtaccac ctttgttttc tttatttcca agtaacaatt taaagccgcc   1080

gccaattaag aggagtgcaa cgatagatgt ttggaaatag cgataatata gctcgctaag   1140

atgaatgtta aatatagttg caaagtaatc attcaaaata gga                     1183
```

<210> SEQ ID NO 27
<211> LENGTH: 756
<212> TYPE: DNA
<213> ORGANISM: Bacillus cereus

<400> SEQUENCE: 27

```
ccaagcacaa caacaggcat atcaagaaca attacaacaa caaggatttg tgaagaaaaa     60

gggatgcaat tgcgggaaaa agaagaacac aataaaacaa tatgaagaat gaaacactca    120

tgctactgtg agtgtttttt attatgtata aaaagcggta tttctgtatt agaaataccg    180

ctttttacta gctaatttgt gcaactgtta atgctgccgc acggatgtct acagttccaa    240

ttaactcaac tggcacaatt tgaattaagt caccaggatt taagttaata agaatgacac    300

cactggatac atctacttca ccagtaccaa taacgttaga acgaactgct gtacctgatc    360

caggaataat attagctggt gtatttaatg ataagaagaa acgaccagct tctggtgcag    420

taggtacgtt atcaagacta attgttaatg tataactaat ttgataaata ccagctcgta    480

gaattcgaat gccatctccg acacttactg tatcgttgat tacaggaaca gtaatatttg    540

ggtttggact tacactaggt aatagtagtg gtgtaaatag tgaagcgaac tgaggtgcag    600

aagcattgaa agcaaaacca aaggcaggta gtgtactagc tggttttgcc tcgcaatcga    660

ttttagtaaa ttcgcaatca gaagagaaca tgtttttcac tcctttatct gtttctactt    720

tcagttaatg aaaaggacag gttctatgtt ctagac                              756
```

<210> SEQ ID NO 28
<211> LENGTH: 535
<212> TYPE: DNA
<213> ORGANISM: Bacillus cereus

<400> SEQUENCE: 28

```
aaaatggata tatttcctat tactttttga aagagatttc ataaattata gtatatcgat     60

tgaaaggagg agatttgaat ggaatttcaa ttgttggtaa cttgtatatt acaagaaggt    120

aatgcttact ttttagtaac gaaggtagat gatgttatta cgttaaaagt accgattact    180

gcgggagtag caggtttatt tttagcttta ggtgtaccaa gatgttctta atttaaatct    240
```

-continued

```
ctatagtaga agaggaaggg acatgtcttc ctttcctact attacataat ataattatgt    300
aaacttaaat atcatatttg tgatagcacg tttgaaatgg acatgcatat actataatgt    360
ttcattggat gttagcggtg aaaggtagtt ttaataagtg catccagtga tatttttaag    420
ctatgaaaat aaaagaggtg ctattatata tgaaaagaaa aacattggat attccagtta    480
cattgcgaag agagtggttt ttaatagagt tagctcattt aacgaaaaaa tatgg         535
```

<210> SEQ ID NO 29
<211> LENGTH: 1392
<212> TYPE: DNA
<213> ORGANISM: Bacillus cereus

<400> SEQUENCE: 29

```
gtttcctatt ttaagtcaat atataacata tttttttaca actttatgat ccttataata     60
ggaaaaactc aaatataaaa caagtaagga ggacataaat gacaaacaat aattgttttg    120
gtcataacca ctgcaataat ccgattgttt tcactccaga ttgctgtaac aatccacaaa    180
cagttccaat tactagtgag caattaggta gattaattac tttactaaac tctttaatag    240
cggctattgc agcgtttttt gcaaatccaa gtgatgcaaa cagattagct ttactcaatt    300
tgtttactca actattgaac ttactaaatg aattagcacc ttccccagaa gggaatttct    360
taaaacaatt aattcaaagt attattaatt tactacaatc tcctaaccca aatctaagtc    420
aattactttc tttattacaa caattctaca gtgctcttgc accattcttc ttctctttaa    480
ttattgaccc tgcaagttta caacttttat taaacttatt aactcaatta attggtgcta    540
ctccaggagg cggagcaaca ggtccaacag gtccaacagg tccaggaggc ggagcaacag    600
gtccaacagg tccaacaggt ccaggaggcg gagcgacagg tccaacaggc ccaacaggag    660
cgacaggtcc agcaggtact ggtggagcaa caggtttaac aggagcaaca ggtttaacag    720
gagcaacagg cttaacagga gcgacaggcc caacgggagc aacaggttta acaggagcaa    780
caggtttaac aggagcaaca ggcttaacag gagcgacagg tccaacagga gcaacaggtc    840
caacaggagc aacaggttta acaggagcaa ctggtgcaac tggtggcgga gctattattc    900
catttgcttc aggtacaaca ccatctgcgt tagttaacgc gttaatagct aatacaggaa    960
ctcttcttgg atttggattt agtcagcctg gtgtagcttt aactggtgga acaagtatca   1020
cattagcatt aggtgtaggt gattatgcat ttgtagcacc acgcgcaggg gttattacgt   1080
cattagctgg tttctttagt gcaacagctg cattagctcc attatcacct gttcaagtgc   1140
aaatacaaat attaactgca cctgcagcaa gcaatacgtt tacagtacaa ggcgcacctc   1200
ttttattaac accagcattt gccgcaatag cgattggttc tacagcatca ggaatcatac   1260
ctgaagctat tccagtagca gctggggata aaatactgtt atatgtttca ttaacagcag   1320
caagtccaat agctgcagtt gctggatttg taagtgcagg tattaatatc gtttaatttg   1380
ttacaatgtt ta                                                       1392
```

<210> SEQ ID NO 30
<211> LENGTH: 1411
<212> TYPE: DNA
<213> ORGANISM: Bacillus cereus

<400> SEQUENCE: 30

```
gaaaacactc aactataaga aaagtaagga ggaaataaat gaaacataat gattgttttg     60
atcataataa ctgcaatccg attgtttttt cagcagattg ttgtaaaaat ccacagtcag    120
ttcctattac tagggaacaa ttaagtcaat taattacttt actaaactca ttagtatcag    180
```

```
ctatttcagc attttttgca aatccaagta atgcaaacag attagtgtta ctcgatttat    240

ttaatcaatt tttaattttc ttaaattcct tattaccttc cccagaagtt aatttttttga   300

aacaattaac tcaaagtatt atagttttat tacaatctcc agcacctaat ttaggacaat    360

tgtcaacatt attgcaacaa ttttatagcg cccttgcaca attcttcttc gctttagatc    420

ttatccctat atcctgcaac tcaaatgttg attctgcaac tttacaactt ctttttaatt    480

tattaattca attaatcaat gctactccag gggcgacagg tccaacaggt ccaacaggtc    540

caacaggtcc aacgggccca gcaggaaccg gagcaggtcc aacgggagca acgggagcaa    600

caggagcaac aggcccaaca ggagcgacag gtccagcagg tactggtgga gcaacaggag    660

caacaggagc aacaggagta acaggagcaa caggggcaac aggagcaaca ggtccaacag    720

gtccaacagg ggcaacaggt ccaacagggg caacaggagc aacaggagca acaggtccaa    780

caggagcaac aggtccaaca ggggcaacgg gcttaacagg agcaactggt gcagctggtg    840

gcggagctat tattccattt gcttcaggta caacaccatc tgcgttagtt aacgcgttag    900

tagctaatac aggaactctt cttggatttg gatttagtca gcctggtgta gcattaacag    960

gtggaactag tatcacatta gcattaggtg taggtgatta tgcatttgta gcaccacgtg   1020

caggaactat cacgtcatta gcaggtttct ttagtgcaac agctgcatta gctccaatat   1080

cacctgttca agtgcaaata caaatattaa ctgcacctgc agcaagcaat acgtttacag   1140

tacaaggcgc acctctttta ttaacaccag catttgccgc aatagcgatt ggttctacag   1200

catcaggtat catagctgaa gctattccag tagctgctgg agataaaata ctactgtatg   1260

tttcattaac agcagcaagt ccaatagctg cagttgctgg atttgtaagt gcaggtatta   1320

atatcgttta atttgttaca atgtttagta ggaaattaaa caggggtttg tatatagtcc   1380

ctcctaaata aatttaggaa ggactatatt t                                 1411
```

<210> SEQ ID NO 31
<211> LENGTH: 822
<212> TYPE: DNA
<213> ORGANISM: Bacillus cereus

<400> SEQUENCE: 31

```
aaatagtatg agagatatta ggttgtctat agatgatatc caatcgatta gtatggccgg     60

tttttaaata tgtaaaggtg gtagaaagct tctaccaccc caatagtttt ttagtttact    120

ttacgataga aacgtcgcgt aagcattgaa tcgcacagaa acagcttaaa tcaacagtaa    180

tgcaagtagt tgtagatatt aatcttgcat ttggtacagc taaaaacgta caaattggat    240

cgtcaccagg tggtactgga gaactgtcac ctaatactac agttaataca cgtagcacag    300

cacagctatc atcatctaca ctttccacac ggaaaattgg agatcggcag ctagtaaggc    360

ttgctgatgg tgcgaatgct tcaaaaggtt ctccagtttt tgtgtataaa ataaaagggc    420

gtgtatttgc tactgatgca gtattgtgtg cacctaaaaa tgggatttca caaccagatc    480

cacatgttgt tgtagaacaa tcttgtaatt cattgatgaa ttttacaacg tcaactacac    540

aatgagaaga gccatggtgt ttattttcgt tacaactcat taatgtcact ccttatcttc    600

ttgtttgtat ttacattaat aagatattgg agtcgaggag atttggtcac aatctcaaga    660

ccttttttttt taaataggcg aaagaggata agggaaggtg aaattatgct gtttacaagc   720

tggcttttat tttttatttt cgcgttagca gcttttaggc tcactcgttt aattgtatat    780

gataaaataa cagccttttt gcgaagacca tttattgatg aa                       822
```

<210> SEQ ID NO 32

-continued

```
<211> LENGTH: 34
<212> TYPE: DNA
<213> ORGANISM: Artificial
<220> FEATURE:
<223> OTHER INFORMATION: PCR primer BclA1

<400> SEQUENCE: 32

ccgagctcgt cgacatgtca aataataatt attc                            34


<210> SEQ ID NO 33
<211> LENGTH: 38
<212> TYPE: DNA
<213> ORGANISM: Artificial
<220> FEATURE:
<223> OTHER INFORMATION: PCR primer BclA2

<400> SEQUENCE: 33

tccccgcggg ctagcagcaa ctttttcaat aataatgg                        38
```

METHOD FOR WHOLE SURROUNDING SURFACE DISPLAY OF TARGET PROTEINS USING BACTERIAL EXOSPORIUM

CROSS-REFERENCE TO RELATED APPLICATIONS

This application is filed under the provisions of 35 U.S.C. §371 and claims the benefit of priority of International Patent Application No. PCT/KR2003/002882 filed Dec. 30, 2003, which in turn claims priority of Korean Patent Application No. 10-2003-0064998 filed Sep. 19, 2003. The disclosures of said applications are hereby incorporated herein by reference in their respective entireties.

TECHNICAL FIELD

The present invention relates to a method for expressing a target protein on an exosporium forming the outermost surface of bacterial spores. More particularly, the present invention relates to a method for expressing a target protein on the surface of cells and spores using an exosporium as a matrix for surface expression, and methods for the production of a protein array, the production of antibodies, the separation of a certain substance from a mixture, bioconversion, and the improvement of a target protein, which are characterized by using the cells or spores having the target protein that was expressed on their surface by the above expression method.

BACKGROUND ART

Surface display technology, where a protein, such as peptide and polypeptide, is attached and expressed on the surface of organism, can be applied to a variety of bioengineering fields according to the properties of the expressed protein or, the properties of host cells, on the surface of which the protein will be expressed (Georgiou et al., *TIBTECH,* 11:6-10, 1993; *Nature Biotechnol.,* 15:29-34, 1997; and Lee et al., *TIBTECH,* 21:45-52, 2003). This surface display technology was developed using various cellular organisms, such as bacteriophages, bacteria, yeasts or mammal cells, as host cells.

In order to express a foreign protein on the surface of cells using the outer membrane protein of a certain organism, a suitable surface protein and the foreign protein should be linked with each other at a gene level to biosynthesize a fusion protein, and stably passed through a cell inner membrane and attached, and then maintained on the cell surface. For this purpose, a protein having the following properties is preferably selected for use as a matrix for surface expression. Namely, (1) it has a secretion signal capable of passing through the cell inner membrane, at the N-terminal end; (2) it must have a targeting signal which can be stably attached on a cell outer membrane; (3) it can be expressed on the cell surface in large amounts within the range having no adverse effect on the growth of cells, such that the protein can show high activity; and (4) it must be able to be stably expressed regardless of its size such that it can be used in various reactions (Georgiou et al., *TIBTECH,* 11:6-10, 1993). Such a matrix for surface expression needs to be genetically engineered such that it is inserted into the N-terminal end, C-terminal end or central portion of the outer membrane protein on the surface of the host cells (Lee et al., *TIBTECH,* 21:45-52, 2003).

Phage surface display technology became very important, since it is advantageous in most rapidly obtaining monoclonal mutants from a large amount of a library ($10^6$-$10^{12}$ mutants) and thus applied to the ultra-high speed screening of antibodies. However, in the phage surface display technology, the level of surface expression of the screened antibodies from a library expressed on the surface of phages was very low. Also, in a surface expression system for gram-negative bacteria, the insertion of a foreign polypeptide resulted in a structural limitation such that stable membrane proteins could not be formed (Charbit et al., *J. Immunol.,* 139:1644-58, 1987; and Agterberg et al., *Gene,* 88:37-45, 1990). Also, the stability and viability of the surface of host cells were reduced. *E. coli* hosts, on which the surface expression technology have been most intensively studied, was developed using a cell surface protein as matrix for surface expression, but had a disadvantage in that if the cell surface protein is over-expressed in a fused form with a foreign protein, the cell surface becomes structurally unstable and thus the viability of the host cells is reduced (Georgiou et al., *Protein Eng.,* 9:239-47, 1996).

Meanwhile, spores are formed in vegetative cells during the growth terminating stage to break the vegetative cells, and then be exposed extracellularly. These spores are structurally uniform, stable, and have resistance to adverse effects of surroundings, such as ultraviolet rays, radiations, heat, toxic compounds and solvents, and thus can be used in various fields. Furthermore, when the environment suitable for cell growth is reached, the spores are germinated again and continued to grow to make it easy to amplify and collect.

There are a large number of cases where a spore coat protein is used as an expression matrix to express target proteins on the spore surface of microorganisms. Examples of such cases include: a case where β-galactosidase for which lacZ as a reporter gene codes is expressed on the surface of spore in a fused form with the outer shell coat protein (CotC) or inner shell coat protein (CotD) of *Bacillus subtilis* (U.S. Pat. No. 5,766,914; U.S. Pat. No. 5,837,500; and U.S. Pat. No. 5,800,821); a case where bacteria and viral/pathogenic antigens are surface-expressed using coat proteins, including CotC, CotD, CotA, CotB, CotE, CotF, CotG, CotN, CotS, CotT, CotV, CotW, CotX, CotY, and CotZ, as a matrix for spore surface display (US 2002/0150594 A1); and a case where target proteins are expressed on the surface of *Bacillus subtilis* spores, using coat proteins, including CotE, CotG, CotA, CotB, CotC, CotD, CotF, CotH, CotJA, CotJC, CotK, CotL, CotM, CotS, CotT, CotV, CotW, CotX, CotY, CotZ, SpoIVA, SpoVID, and SodA, as a matrix for spore surface display (WO 02/46388).

However, if the spore coat protein is used as the expression matrix, a fusion protein with the surface expression matrix should be made for the surface expression of target proteins, but there is a disadvantage in that the expression level of the fusion protein is low since one of various coat proteins is used as a matrix for surface expression. Also, the level of the surface expression of the target protein using the surface expression matrix and the fusion protein is limited since the target protein is expressed depending on a degree at which the surface expression matrix is inserted into the surface of cells and spores. Furthermore, if the target protein is over-expressed, there are problems in that the structural deformation of the spores can be caused or the inherent physical and chemical properties of the spores can be greatly changed, so that the viability or resistance to environment of the host cells can be greatly reduced.

Accordingly, the present inventors have conducted intensive studies in an attempt to solve the problems occurring in the above-mentioned spore surface display technology of the prior art, and consequently found that if a target protein was expressed on the cell or spore surface using the structurally stable exosporium of *Bacillus subtilis* as a matrix for surface expression, the target protein fused with the exosporium can be surface-expressed without changing the inherent structure of cells or spores even when the target protein is over-expressed, so that the viability or resistance to environment of the gene carriers (cells or spores) is not changed, thereby perfecting the present invention.

Since the exosporium is present on the outermost surface of a spore, it can show the effect of surrounding the whole spore by a target protein upon spore surface display without influencing the structure of the coat protein of a spore. Moreover, it can also be used in the cell surface expression of bacteria, including gram-positive or gram-negative bacteria using an exosporium protein. It has not yet been reported that a target protein can be expressed on the surface of cells or spores using the exosporium of the *Bacillus cereus* group was not yet reported. The *Bacillus cereus* group, which generally includes *Bacillus thuringiensis* and *Bacillus anthracis*, possesses a loose balloon-like exosporium, which has also been found in some other bacilli and clostridia (Desrosier, J. P. and J. C. Lara, *J. Gen. Microbiol.,* 130:935-40, 1984).

If this exosporium is used in the surface expression of a target protein, the target protein will not influence the spore coat protein and thus will not cause the structural problem. Also, the amount of the target protein expressed on the spore surface is increased, and the viability or resistance to environment of a host cell will not be changed even when the amount of the target protein expressed on the outer membrane of the spores is increased.

DISCLOSURE OF INVENTION

Therefore, a main object of the present invention is to provide a method of expressing a target protein on the spore or cell surface, in which the target protein is expressed on the spore or cell surface using an exosporium as a matrix for surface expression.

Another object of the present invention is to provide a method for producing a protein array, a method for producing antibodies in vertebrata, a bioconversion method, and a method for separating a certain substance from a mixture, which are characterized by using the cells or spores that are produced by the above expression method and have the target protein expressed on their surface.

To achieve the above object, the present invention provides a method for expressing a target protein on the surface of cells or spores, the method comprising the steps of: (a) selecting a gene encoding an exosporium; (b) constructing a gene recombinant containing the gene encoding the target protein and a gene encoding the exosporium, or an expression vector comprising the genetic recombinant, such that the target protein is expressed in a fused form with the exosporium; (c) transforming microbial host cells with the gene recombinant or the expression vector, the microbial host cells being selected from the group consisting of gram-negative bacteria, gram-positive bacteria, *Actinomyces*, yeasts, and molds; (d) culturing the transformed host cells to express the target protein in the host cells or on the spore surface of the host cells; and (e) collecting the cells or spores having the target protein expressed on their surface.

Also, the present invention provides a method for producing a protein array, the method comprising the step of attaching the cells or spores, which are produced by the above expression method and have the target protein expressed on their surface, on the surface of a substrate.

As used herein, the term "protein array" is intended to include a protein chip, a bioMEMS, and a pattern of cells or spores, in which a protein is immobilized on a solid substrate.

Furthermore, the present invention provides a method for producing an antibody in Vertebrata, the method comprising the steps of: administering the cells or spores, which are produced by the above expression method and have an antigen expressed on their surface, to the Vertebrata excluding a man; inducing an immune response in the Vertebrata; and recovering the antibody produced by the immune response.

Moreover, the present invention provides a bioconversion method, which is characterized by using the cells or spores which are produced by the above expression method and have the target protein having an enzymatic activity, expressed on their surface. As the surface-expressed substances of catalyzing chemical reaction, any substances capable of catalyzing chemical reaction, such as enzymes and catalytic antibodies, are surface-expressed in a fused form with the exosporium and can be used in the chemical reaction.

Also, the present invention provides a method for separating a certain substance from a mixture, the method comprising the step of contacting the cells or spores, which are produced by the above expression method and have a binding domain expressed on their surface, with the mixture.

Furthermore, the present invention provides a surface expression vector which comprises a replication origin, an antibiotic-resistant gene, a restriction enzyme site, an exosporium gene and a gene encoding a target protein, and comprises a gene recombinant constructed to be expressed on the spore or cell surface in a fused form with the exosporium when the gene encoding the target protein is expressed in a host cell.

Moreover, the present invention provides a recombinant microorganism which is obtained by transforming a microorganism selected from the group consisting of gram-negative bacteria, gram-positive bacteria, *Actinomyces*, yeasts, and molds, with the expression vector or a gene recombinant, which comprises a gene encoding a target protein and is constructed to can be expressed on the spore or cell surface in a fused form with an exosporium when the gene encoding the target protein is expressed in a host cell.

Also, the present invention provides a protein complex which is produced by the above expression method and in which a target protein is expressed on the spore or cell surface in a fused form with an exosporium. The present invention also provides a protein array in which the protein complex is attached on the surface of a substrate.

Furthermore, the present invention provides a method for improving a target protein, the method comprising the steps of: (a) selecting a gene encoding an exosporium; (b) establishing a mutant library of a gene encoding the target protein; (c) constructing a gene recombinant containing the mutant library of the gene encoding the target protein and the gene encoding the exosporium, such that the mutant of the target protein is expressed in a fused form with the exosporium; (d) transforming microbial host cells selected from the group consisting of gram-negative bacteria, gram-positive bacteria, *Actinomyces*, yeasts, and molds, with the gene recombinant or the expression vector containing the gene recombinant; (e) culturing the transformed host cells to express the gene mutant library on the spore or cell surface; and (f) screening spores or cells where the target protein having improved characteristics was expressed.

Also, the present invention provides a method for improving a target protein using the resistance of spores, the method comprising the steps of: (a) establishing a mutant library of a gene encoding a target protein; (b) constructing a gene recombinant containing the mutant library of the gene encoding the target protein and a gene encoding an exosporium, such that the mutant of the target protein is expressed in a fused form with the exosporium; (c) transforming microbial host cells selected from the group consisting of gram-negative bacteria, gram-positive bacteria, *Actinomyces*, yeasts, and mold, with the gene recombinant or an expression vector containing the gene recombinant; (d) culturing the transformed host cells to obtain a spore library having the gene mutant library expressed on its surface; (e) treating the spores having the target protein mutant expressed on their surface, with means selected from the group consisting of organic solvents, heat, acids, bases, oxidizing agents, drying, surfactants and proteases; (f) screening the spores where the target protein mutant having resistance to the treatment was expressed on the spore surface; and (g) culturing the screened spores in a suitable medium to collect a mutant of the target protein with the desired characteristics or a gene encoding the mutant.

In addition, the present invention provides a method for improving a target protein using the resistance of spores, the method comprising the steps of: (a) establishing a mutant library of a gene encoding a target protein; (b) constructing a gene recombinant containing the mutant library of the gene encoding the target protein and a gene encoding an exosporium, such that the mutant of the target protein is expressed in a fused form with the exosporium; (c) transforming microbial host cells selected from the group consisting of gram-negative bacteria, gram-positive bacteria, *Actinomyces*, yeasts and molds, with the gene recombinant or an expression vector containing the gene recombinant; (d) culturing the transformed host cells to obtain a spore library having the gene mutant library expressed on its surface; (e) treating the spores having the target protein mutant expressed on their surface, with means selected from the group consisting of organic solvents, heat, acids, bases, oxidizing agents, drying, surfactants and proteases; (f) treating the treated spores with a given amount of protease; (g) screening the spores where the target protein mutant with resistance to the protease was expressed on the spore surface; and (h) culturing the screened spores in a suitable medium to collect a target protein mutant having the desired characteristics, or a gene encoding the target protein mutant.

In the protein improvement method of the present invention, the screening step is performed by using any one selected from the group consisting of an activity of the target protein, a protein recognizing a substance labeled to the target protein, a labeled ligand binding to the target protein, and an antibody specifically binding to the target protein, in which the screening step either using the labeled ligand binding to the target protein or using the antibody specifically binding to the target protein is performed with a flow cytometer.

In all the surface expression technologies known till now, the target protein is surface-expressed using one or several surface proteins so that the surface structure of cells or spores can be modified. On the other hand, the present invention provides a new surface expression method, wherein an outer membrane protein and a target protein are fused on the outermost surface of a spore as a gene carrier other than the coat protein of the spore and expressed inside or outside the host cell, so that the target protein can be naturally surface-expressed in a form surrounded by the gene carrier.

In the present invention, the cell as the gene carrier is a microorganism, particularly any one selected from the group consisting of gram-negative bacteria, gram-positive bacteria, *Actinomyces*, yeasts and molds. In a preferred embodiment of the present invention, a host cell for the surface expression on the spore outer membrane is derived from spore-forming gram-negative bacteria, including *Myxococcus*; spore-forming gram-positive bacteria, including *Bacillus*; and spore-forming *Actinomyces*; spore-forming yeasts or molds, including *Saccharomyces cerevisiae*, genus *Candida*, genus *Hansenulla*, but is not limited thereto. More preferably, the host cell for the surface expression on the spore outer membrane is derived from spore-forming gram-positive bacteria, and most preferably, from the *Bacillus cereus* group, including *Bacillus thuringiensis, Bacillus anthracis* and *Bacillus cereus*, and genus *Bacillus* including *Bacillus subtilis.*

Meanwhile, the *Bacillus cereus* group has a characteristic in that it forms an exosporium outside the spore coat, unlike a *Bacillus subtilis* spore. Thus, in the present invention, a gene encoding the exosporium is preferably derived from the *Bacillus cereus* group. Also, the *Bacillus cereus* group is advantageous for use in the present invention, since its genetic information is known at large amounts and its culturing method is well known. FIG. 1 is a schematic view showing that the target protein according to the present invention is expressed on the surface of the spore outer membrane.

In the method of the present invention, when the target protein is expressed intracellularly or extracellularly, it may be one target protein gene, target protein genes, repeated two times or more, which are the same or different from each other, or any combination thereof.

It is obvious to a person skilled in the art that the gene produced in the inventive method can be independently present within a plasmid in a host cell or in a form inserted into the host chromosome.

Meanwhile, it is obvious to a person skilled in the art that the target protein can be expressed by one of the following promoters: a promoter whose expression can be induced in a host cell; a target protein gene promoter; and other suitable promoters which can be expressed in host bacteria.

The method of the present invention can be applied to all proteins, and used for the surface expression and improvement of proteins, such as enzymes, enzyme inhibitors, hormones, hormone analogues, antibodies, signal transfer proteins, single-chain antibodies, antigens, peptides, polypeptides, binding proteins, binding domains, adhesion proteins, structural proteins, regulatory proteins, toxin proteins, cytokines, various regulators, proteins containing a portion thereof.

In the method of the present invention, there can be used all spores that can or cannot be reproduced. In the case where a protein is improved by the surface expression method using the outer membrane protein of spores, the collected spores should be reproduced, but in the case where the spore is used as a simple means for transferring the target protein, the spore doesn't have to be reproduced. Since a spore that is regarded particularly as a genetically engineered organism can be regulated in use, it is preferable to use a mutant strain that cannot be reproduced. In the present invention, there can be used, for example, a gerN gene-deleted, non-reproducible mutant strain of *Bacillus cereus*, a gerX gene-deleted, non-reproducible mutant strain of *Bacillus anthracis*, and a cwlD, rec223, gerA, gerB, gerC, or gerD gene-deleted, non-reproducible mutant strain of *Bacillus subtilis.*

The fact that a protein was finally expressed on the surface of the spore outer membrane by the expression method of the present invention can be proved by the various following methods. First, a primary antibody is bound to a protein expressed on the surface of the spore outer membrane, and a secondary antibody labeled with a fluorescent compound is reacted to fluorescently stain the spore, and then, the spore can be observed with a fluorescent microscope or analyzed with a flow cytometer. If the secondary antibody is labeled with gold, the spore can be observed with an electronic microscope. In the second method, observation is performed on whether the surface-expressed protein is degraded by the protease introduced from the outside, to reduce enzyme activity, or its signal is reduced in a fluorescent microscope or a flow cytometer. Third, if the target protein is an enzyme that utilizes a polymer substance as a substrate, the substrate cannot pass through the spore outer shell structure upon the measurement of the enzyme activity. Thus, it can be found that all the measured enzyme activities are attributed to the enzyme exposed to the surface.

A protein array, such as a DNA array or a DNA chip, arrays various proteins, particularly antibodies, on a solid surface, so that it provides a means capable of analyzing the expression and expression level of the desired target protein in certain cells. In an analysis process using the protein array, in order to bind to immobilized proteins and to wash unbound proteins, various treatments, such as heating and changes in salt concentration and pH, are conducted, and thus, the immobilization of a stabilized protein capable of resisting this severe environment is required. However, in cloning several thousands to several ten thousands of genes into an expression vector, and expressing and separating them and then immobilizing them on a solid surface, many operations should be conducted in a repeated manner. Thus, such operations need to be conducted in a more simple and rapid manner.

The method for producing the protein array according to the present invention provides a means allowing such operations to be most easy. According to the inventive method, the gene recombinant containing the gene encoding the target protein and the gene encoding the exosporium is introduced into host cell, and the spore having the target protein expressed on the surface of its outer membrane is separated and then immobilized on a solid surface. For the production of the protein array according to the present invention, the method which is conventionally used in the art can be applied (WO 00/61806; WO 00/54046; U.S. Pat. No. 5,807,754; EP 0818467; WO 97/42507; U.S. Pat. No. 5,114,674; and WO 96/35953). The protein array produced by the inventive method can be used in a diagnostic kit, gene expression analysis, the analysis of protein-protein, protein-ligand or antigen-antibody interaction, metabolic process analysis, the screening of a new enzyme or improved enzyme, combinatorial biochemical synthesis, and biosensors. In order to immobilize a protein on a substrate, it is preferable that a linker molecule is also attached and the remaining portion that was not spotted is blocked. Meanwhile, the amount of the spore having a target protein expressed on the surface of its outer membrane, which are applied to each spot, is determined depending on an array form.

A method for forming a BioMEMS and patterning proteins provides a means capable of analyzing the expression and expression level of a target protein in a cell or spore on a solid surface. The obtained target protein should be immobilized on the solid surface. For this, various treatments, such as heating and changes in salt concentration and pH, are conducted, and thus, the immobilization of a stabilized protein capable of resisting this severe environment is required. According to the method of forming the bioMEMS and pattern of the present invention, the gene recombinant containing the gene encoding the target protein and the gene encoding the exosporium is introduced into host cell, and the gene carrier, which was surface-expressed on the exosporium, is separated and then immobilized on a solid surface. The method which is conventionally used in the art can be applied to forming the bioMEMS and pattern of the present invention (WO 00/61806; WO 00/54046; U.S. Pat. No. 5,807,754; EP 0818467; WO 97/42507; U.S. Pat. No. 5,114,674 and WO 96/35953). The bioMEMS and pattern produced by the inventive method can be used in a diagnostic kit, gene expression analysis, the analysis of protein-protein, protein-ligand or antigen-antibody interaction, the screening of a new enzyme or improved enzyme, metabolic process analysis, combinatorial biochemical synthesis and biosensors, etc.

In the method for the improvement of a target protein according to the present invention, the gene library can be obtained by modifying the gene of a wild-type target protein using DNA shuffling (Stemmer, *Nature,* 370:389-91, 1994), StEP (Zhao, H. et al., *Nat. Biotechnol.,* 16: 258-61, 1998), RPR (Shao, Z. et al., *Nucleic Acids Res.,* 26:681-3, 1998), molecular breeding (Ness, J. E. et al., *Nat. Biotechnol.,* 17:893-6, 1999), ITCHY (Lutz, S. et al., *Cur. Opi. Biotechnol.,* 11:319-24, 2000), error-prone PCR (Cadwell, R. C. et al., *PCR Methods Appl.,* 2:28-33, 1992), and point mutation (Sambrook et al., *Molecular Cloning: A Laboratory Manual*, Cold Spring Harbor, N.Y., 1989), but is not limited thereto.

In the protein improvement method of the present invention, the screening step can be rapidly conducted by measuring the activity of a protein or using a flow cytometer (Georgiou, G., *Adv. Protein Chem.,* 55:293-315, 2000). In the case of measuring the protein activity, the screening can be achieved by either measuring the growth of a host in which a protein is expressed, or measuring the color development reaction catalyzed by the protein. Furthermore, in the inventive method using the resistance of a spore, the screening step can be rapidly performed by using the protein activity or the stability of a protein structure.

In the case of using the inventive protein improvement method having the above characteristics, an enzyme catalyzing chemical reaction that does not occur biologically (e.g., Diels-Alder condensation), an enzyme with unnatural stereoselectivity or regioselectivity, an enzyme capable of catalyzing reaction in an organic solvent or a higher solution than organic solvent-aqueous solution, and an enzyme catalyzing reaction in extreme conditions such as high temperature and high pressure, etc., which cannot be easily obtained by the prior method, can be rapidly obtained from wild-type enzymes. Also, in the case where the elution of bacteria is conducted with rapid pH change or base concentration control, which is applied to screening an antibody mutant with increased binding force, there is a disadvantage in that the survival rate of the bacteria is reduced when the bacteria is re-inoculated in medium. This disadvantage will be solved by the application of the inventive protein improvement method using a spore surface display system.

Meanwhile, even when a surface-expressed enzyme is used in a bioconversion process, a host for surface expression must be physically and chemically stable in extreme conditions since reaction is performed in high temperature and/or organic solvent. Particularly, an industrial important recent chemical synthesis reaction is frequently conducted in an organic solvent, and the synthesis of a chiral compound and the decomposition of the chiral compound from a racemic mixture must be conducted in very severe physical and chemical environments. Thus, a surface-expressed enzyme must be stable under such extreme conditions, and also an organism having this enzyme expressed on its surface must be stable. In terms of this point, the inventive bioconversion method using a system of expressing a protein on the surface of the spore's outer membrane is particularly advantageous.

Meanwhile, a chemical reaction process using a surface-expressed catalyst was proposed (Georgiou et al., *TIBTECH,* 11:6-10, 1993). However, if the surface-expressed catalyst was used, a surface-expressed host cell is unstable during the reaction process so that the cell surface needed to be immobilized with cross-linking chemicals (Freeman et al., *Biotechnol. Bioeng.,* 62:155-9, 1999). The bioconversion method of the present invention solves the above problems. In the inventive method, since a catalyst expressed on the surface of the spore outer membrane is used, the spore itself as well as the surface-expressed catalyst is stable and thus do not need to be specially immobilized. Although the bioconversion reaction using beta-galactosidase is illustrated in Examples below, it is obvious to a person skilled in the art from the disclosure in the specification that the inventive method can utilize any enzyme expressed on the spore surface, including lipase, protease, cellulase, glycosyltransferase, oxidoreductase and aldolase. Moreover, the inventive method can also be applied to the case where the bioconversion reaction is a single-stage or multi-stage reaction and occurs in an aqueous solution or non-aqueous solution phase, and the spore can be used in an immobilized or non-immobilized state and also in combination with other microorganisms or enzymes.

The surface expression technology as described above expresses an antigen or a part thereof on the cell surface to produce an antibody so that it provides a transfer means of recombinant live vaccine using the same. In the vaccines developed till now, attenuated pathogenic bacteria or viruses were mainly used, and in the case of the bacteria, an antigen was secreted and expressed inside a cell, on a cell membrane, or outside a cell, and transferred to a host cell. Since the surface-expressed live vaccine shows a very strong immune response and can be grown in a host cell while continuously expressing an antigen, it is noticed as a new vaccine transfer means. Particularly, when a pathogen-derived antigenic epitope is expressed on the surface of non-pathogenic *E. coli* or *Salmonella* sp. and orally administered in a living state, it is known to show a far more lasting and strong immunity, so that it can be used as a method for inducing antigen-antibody production (Georgiou et al., *Nature Biotechnol.,* 15:29-34, 1997; and Lee et al., *Nature Biotechnol.,* 18:645-8, 2000).

Martineau et al., reported a very simple method of producing an antipeptide antibody using the expression technology on the *E. coli* surface (*Bio/Technol.,* 9:170-2, 1991). In this surface expression technology, the desired peptide is expressed on the surface protrusions of MalE and LamB which is a cell outer membrane, and then, the whole cell or ground cell is administered to an animal to induce the production of an anti-peptide antibody. According to this method, the antibody can be produced without chemically synthesizing peptide or attaching it to a transfer protein.

Meanwhile, in order to immobilize an antibody or polypeptide for use in adsorption chromatography on a suitable carrier, the production of a protein by fermentation, the separation and purification of the protein into a pure state, and the immobilization of the protein on a carrier, should be carried out. However, in most cases, a producing process of such a bioadsorbent is not simple. It is reported that such problems can be solved by using the whole cell where enzyme was continuously expressed on the cell surface (Georgiou et al., *Nature Biotechnol.,* 15:29-34, 1997). Thus, the inventive system for the expression on the surface of the spore outer membrane can be applied as a method for the production of the whole cell adsorbent.

The surface expression technology as described above can be used in separating a certain substance from various mixtures. In order to immobilize an antibody or polypeptide for use in adsorption chromatography on a suitable carrier, the production of a protein by fermentation, the separation and purification of the protein into a pure state, and the immobilization of the protein on a carrier, should be carried out.

A technology where an adsorption protein is expressed on a microbial surface, and the resulting whole cell is used as an adsorbent, was developed. An well known example as the whole cell adsorbent is *Staphylococcus aureus*, on the surface of which protein A with high affinity for the Fc domain of a mammalian antibody was naturally expressed. Recently, a new method was proposed, in which a metal-adsorbing protein, such as metallothionein or several histidine residues, is expressed on the cell surface at a large amount using microbial surface expression technology, to remove and collect heavy metals (Sousa et al., *Nature Biotechnol.,* 14:1017-20, 1996; and Samuelson et al., *Appl. Environ. Microbiol.,* 66:1243-8, 2000). According to this method, heavy metals can be removed or recovered from a contamination source in a more effective manner than the prior method using metal-adsorbing microorganisms.

A microbial transformant of the present invention is preferably mutated such that it is suitable for the surface expression on the spore outer membrane. For example, it is preferable that the microbial transformant is either mutated such that a protease that is secreted extracellularly cannot be produced to stably maintain a target protein expressed on the surface of the spore outer membrane, or mutated such that it cannot produce an intracellular protease that degrades the target protein. Furthermore, it is preferable to increase the spore formation rate of a microorganism by the modification of a regulatory gene involved in spore formation (Perego et al., *Mol. Microbiol.,* 19:1151-7, 1996).

The present invention provides a spore for use in the expression of a target protein on the surface of the spore outer membrane, wherein the spore outer membrane has the target protein expressed on its surface. The spore of the present invention can or cannot be reproduced and it can be chosen depending on its purpose, the criterion of which is described above. The spore that cannot be reproduced is preferably produced by one or complex methods with two or more selected from the group consisting of a genetic method (Popham et al., *J. Bacteriol.,* 181:6205-9, 1999), a chemical method (Setlow et al., *J. Appl. Microbiol.,* 89:330-8, 2000) and a physical method (Munakata et al., *Photochem. Photobiol.,* 54:761-8, 1991). The genetic method making spore reproduction impossible preferably comprises deleting the gene involved in spore reproduction of a host cell producing the spore.

Meanwhile, the spores of the present invention are preferably mutated such that they have increased cohesiveness. This is because the spores having increased cohesiveness can be easily separated from a reaction product upon bioconversion reaction. The increase in cohesiveness of the spores can be achieved by heat treatment (Wiencek et al., *Appl. Environ. Microbiol.,* 56:2600-5, 1990), and also other physical, chemical or genetic methods.

DETAILED DESCRIPTION OF THE INVENTION

The present invention will hereinafter be described in further detail by examples. It will however be obvious to a person skilled in the art that these examples are given for illustrative purpose only, and the scope of the present invention is not limited to or by these examples.

Example 1

Construction of Recombinant Vector

In order to express various target proteins on the surface of the spore outer membrane forming the outermost portion of spores, a recombinant vector was constructed in the following manner. First, pDG1662 (BGSC: *Bacillus* Genetic Stock Center, Ohio) was cut with PstI and SalI, and inserted into the same site of pBR322, to produce pTJS7. To insert the replication origin of *Bacillus* into a recombinant vector, PCR was performed using SEQ ID NO: 1 and SEQ ID NO: 2 as primers, and the DNA of *Bacillus subtilis* 168 (BGSC 168) as a template, to obtain the replication origin of *Bacillus*. The obtained DNA and the pTJS7 were cut with EcoRI and PstI, and then linked, to produce pTJSB9. The pTJSB9 was cut with NdeI and SphI and a multi-cloning site (SEQ ID NO: 3) was synthesized and then, inserted into the cut pTJSB9, to construct pSD1 as a recombinant vector. This vector was used in using the multi-cloning site to express an exosporium as described below.

Example 2

Cloning of Exosporium

In order to clone a target protein to be fused with an exosporium forming the outermost portion of spores, a gene recombinant was constructed in the following manner.

Figure 1:
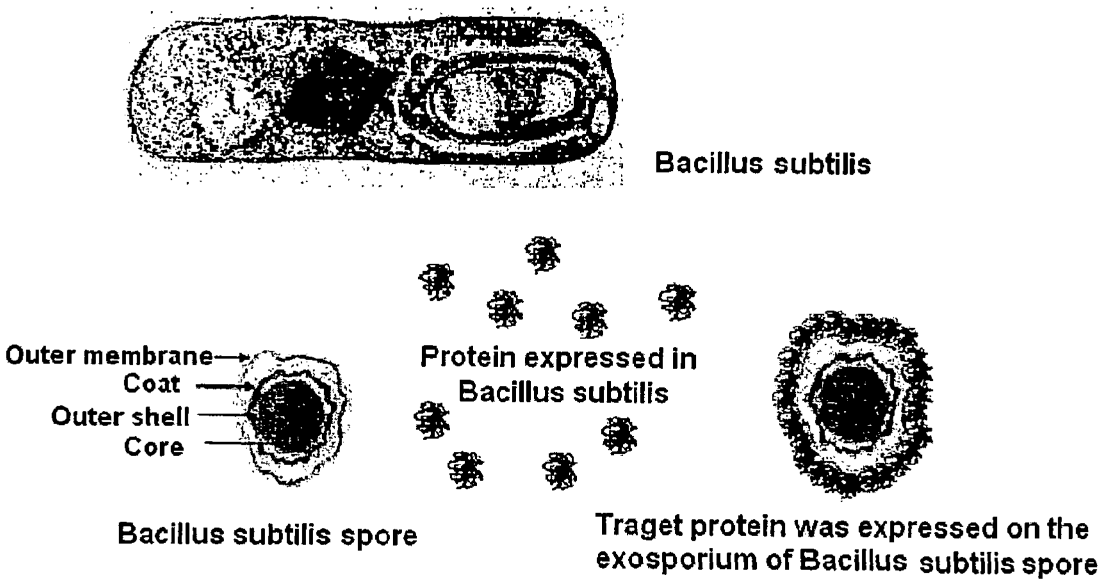
FIG. 1 is a schematic view showing that a target protein was expressed on the surface of the spore outer membrane.
Figure 2:
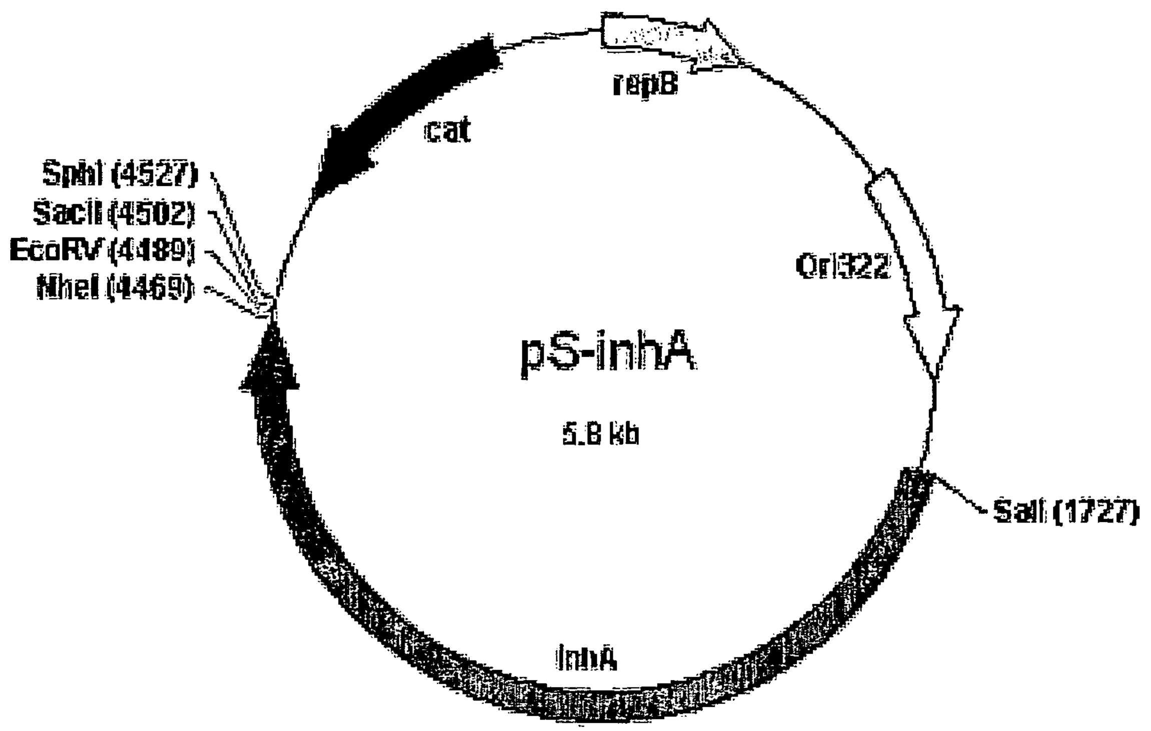
FIG. 2 shows an expression vector (pS-InhA) containing the outer membrane protein gene of *Bacillus thuringiensis* (BT) spores.

The DNA of a *Bacillus thuringiensis israelensis* 4Q7 (BGSC 4Q7) strain was separated by a method of Kalman et al. (*Appl. Environ. Microbiol.,* 59:1131-37, 1993). PCR was performed using the separated DNA (SEQ ID NO: 4) as a template, and primer IAP1 (SEQ ID NO: 5) and primer IAP2 (SEQ ID NO: 6), to amplify an exosporium gene. The PCR product (exosporium gene) was cut with SalI and NheI, and inserted into the same site of the plasmid pSD1 produced in Example 1, to construct pS-InhA (FIG. 2).

Example 3

Expression of Carboxymethylcellulase (CMCase) on Surface of Spore Outer Membrane The fact that a target protein can be expressed on the spore surface using the exosporium of the *Bacillus cereus* group was not yet reported. Since the spore of *Bacillus cereus* group has an outer membrane known as an immune inhibitor at its outermost portion (Edlund et al., *Infect. Immunol.,* 14:934-41, 1976), if a target protein is expressed in a fused form with the spore outer membrane, the surface expression of the target protein will be possible. To prove this fact, the CMCase of *Bacillus* was expressed in a fused form with the *Bacillus thuringiensis* exosporium, and transformed into *Bacillus subtilis* DB104 (Kawamura & Doi, *J. Bacteriol.,* 160: 442-444, 1984) and *Bacillus thuringiensis* 4Q7 (BGSC 4Q7). Then, the transformed strain was cultured in a medium of inducing spore formation, and then the spores were extracted and used for measurement for enzymatic activity.

To express CMCase on the surface of the spore outer membrane, the CMCase gene obtained from a *Bacillus subtilis* 168 strain (BGSC 168) was cloned. To clone the CMCase, the DNA of the *Bacillus subtilis* 168 strain was separated by the method of Kalman et al., and PCR was performed using the separated DNA as a template, and primer INCM-1 (SEQ ID NO: 7) and primer INCM-2 (SEQ ID NO: 8). The PCR product was cut with NheI and KpnI, and inserted into the plasmid pS-InhA produced in Example 2. The resulting plasmid pS-InhA-CMCase was introduced into *Bacillus subtilis* DB104 or *Bacillus thuringiensis* 4Q7.

Then, the transformed *Bacillus subtilis* strain was cultured in a 2×SG medium (16 g/l nutrient broth, 2 g/l KCl, 0.5 g/l $MgSO_4.7H_2O$, 1 ml/l of 1 M $Ca(NO_3)_2.2H_2O$, 1 ml/l of 0.1 M $MnCl_2.4H_2O$, 1 ml/l of 1 mM $FeSO_4$, 1 g/l glucose) for about 48 hours, and the *Bacillus thuringiensis* strain was cultured in the 2×SG medium for about 60 hours, and then only spores were separated by urografin gradients method (Harwood et al., Molecular Biological Methods for *Bacillus*, John Wiley & Sons, N.Y., p. 416, 1990).

The activity of CMCase was measured for the separated spores. For this, 200 μl of 1% (w/v) carboxymethylcellulose solution (0.1M potassium phosphate, pH 6.0) was added to 100 μl of spore solution (0.1M potassium phosphate, pH 6.0) with the absorbance of about 1.5 at 600 nm wavelength, and the mixture was reacted at 50° C. for 40 minutes. On the end of the reaction, 900 μl of DNS solution (1% 3,5-dinitrosalicylic acid, 1% NaOH, 20% sodium potassium tartrate, 0.2% phenol, 0.05% $NaHSO_3$) was added to the reaction solution, and heated for 5 minutes, followed by cooling in cold water.

Figure 3:
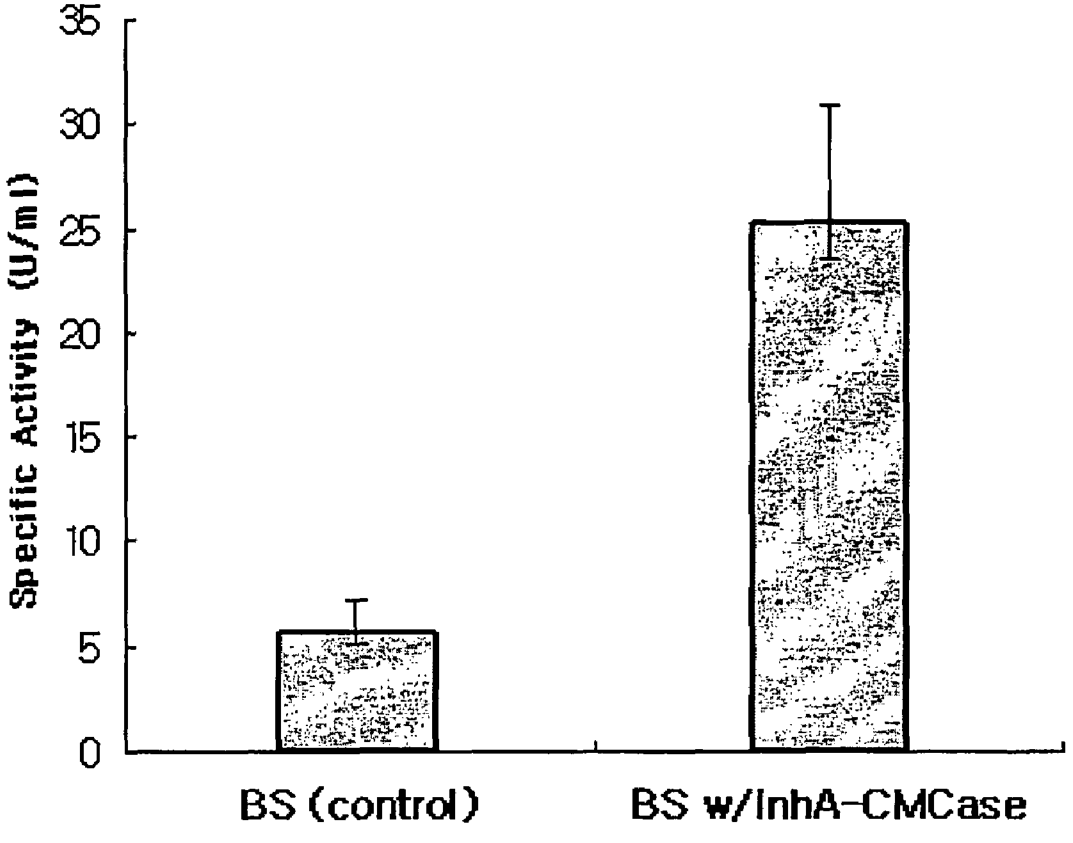
FIG. 3 is a graphic diagram showing the activity of carboxymethyl cellulase expressed on the surface of the outer membrane of *Bacillus subtilis* (BS) spores.
Figure 4:
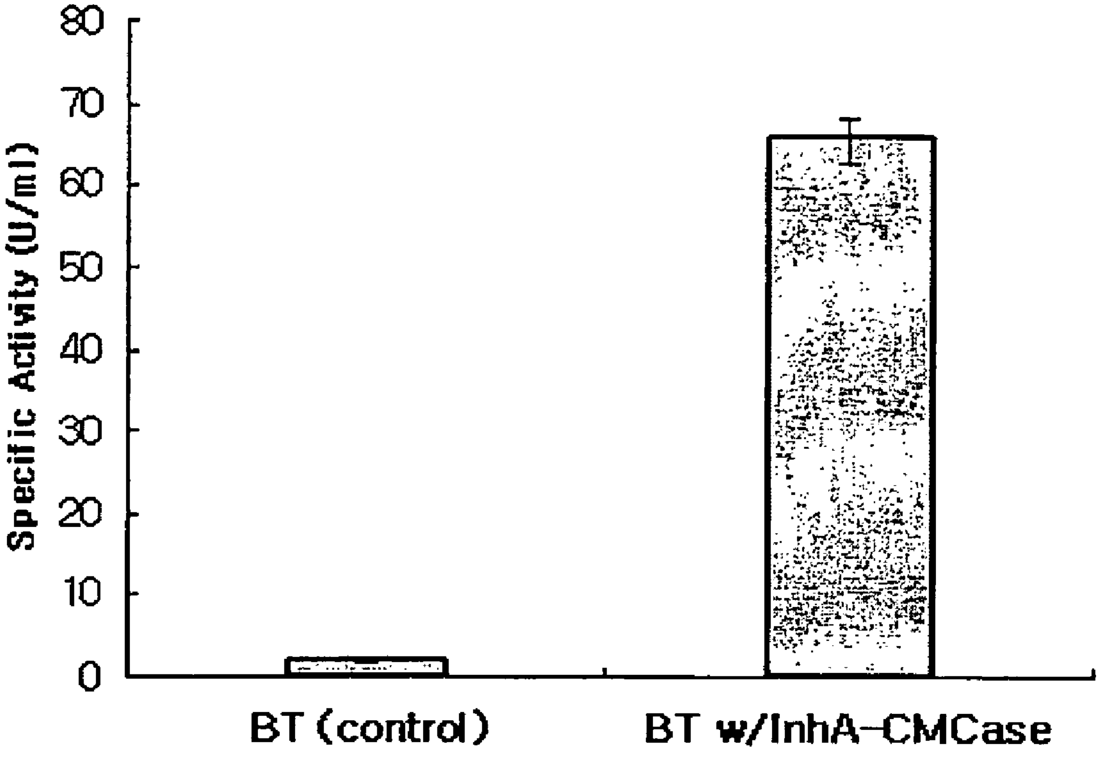
FIG. 4 is a graphic diagram showing the activity of carboxymethyl cellulase expressed on the surface of the outer membrane of *Bacillus thuringiensis* spores.
Figure 5:
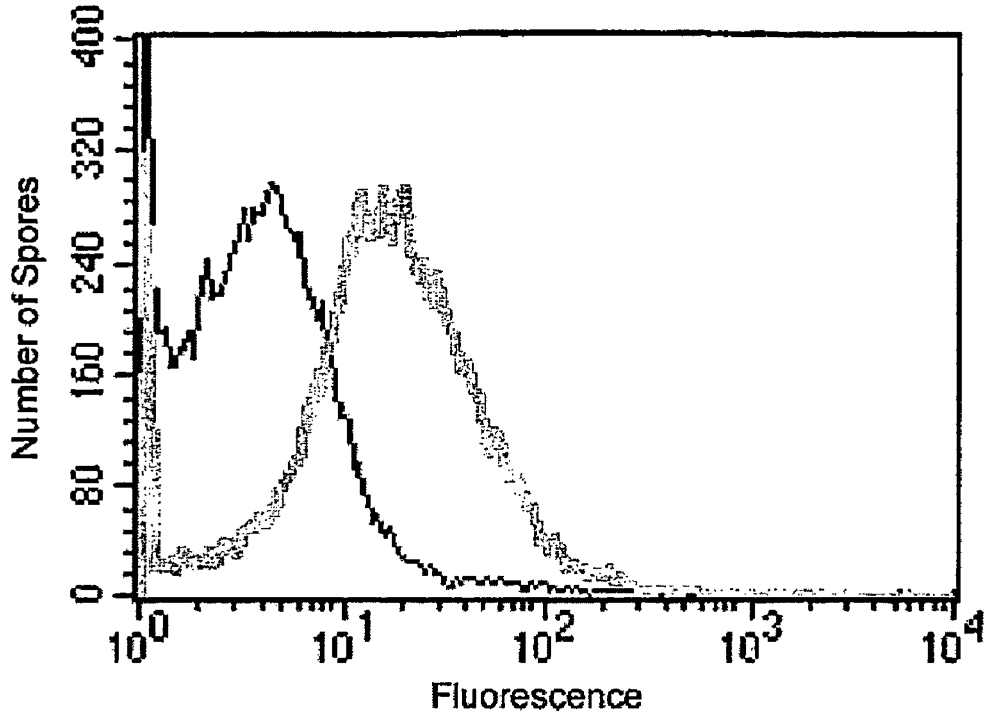
FIG. 5 is a graphic diagram showing the result of analysis using flow cytometer for the expression of CMCase on the surface of the outer membrane of *Bacillus subtilis* spores.
Figure 6:
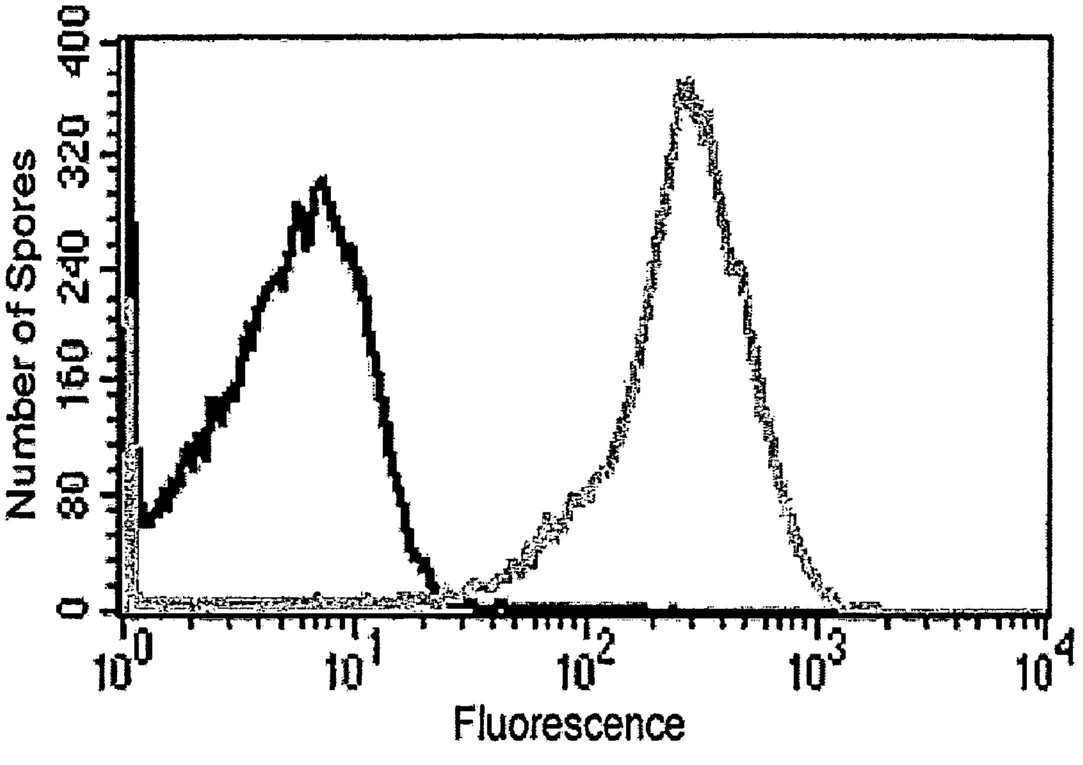
FIG. 6 is a graphic diagram showing the result of analysis using flow cytometer for the expression of CMCase on the surface of the outer membrane of *Bacillus thuringiensis* spores.

The resulting solution was centrifuged and the supernatant was measured for the absorbance at 575 nm wavelength. In *Bacillus subtilis*, the activity of CMCase was 8 mU for a control group (DB104), but 13.5 mU for DB104 w/InhA-CMCase where the enzyme have been expressed on the surface of the spore outer membrane (FIG. 3). In *Bacillus thuringiensis*, the activity of CMCase was 6 mU for a control group (4Q7), but 65 mU for 4Q7 w/InhA-CMCase where the enzyme had been expressed on the surface of the spore outer membrane (FIG. 4). Meanwhile, the strains were analyzed with a flow cytometer (FACSCalibur, Becton Dickinson Co., USA) using an antibody specially binding to CMCase (Kim et al., *Appl. Environ. Microbiol.,* 66:788-93, 2000), and the results showed that CMCase was detected on the surface of the *Bacillus subtilis* spores (FIG. 5) and *Bacillus thuringiensis* spores transformed with pS-InhA-CMCase (FIG. 6).

Example 4

Expression of Beta-Galactosidase on Surface of Spore Outer Membrane

For the expression of β-galactosidase on the surface of the spore outer membrane, the DNA of wild-type *E. coli* K-12 (ATCC 25404) was separated by the method of Kalman et al., and then, PCR was performed using the separated DNA as a template, and primer INLZ-1 (SEQ ID NO: 9) and primer INLZ-2 (SEQ ID NO: 10). The PCR product was cut with NheI and KpnI, and inserted into the plasmid pS-InhA produced in Example 2. The resulting plasmid pS-InhA-LacZ was introduced into *Bacillus subtilis* DB104 or *Bacillus thuringiensis* 4Q7. Then, the transformed *Bacillus subtilis* and *Bacillus thuringiensis* strains were cultured in the same condition as in Example 3, and only pure spores were separated.

Figure 7:
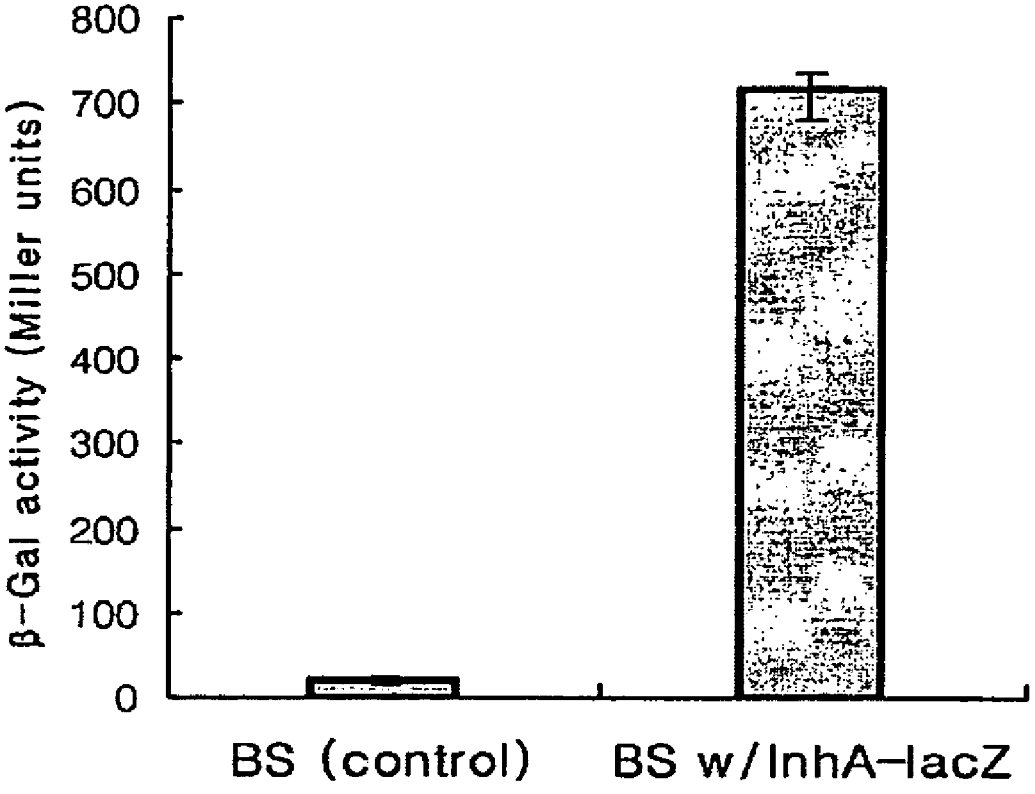
FIG. 7 is a graphic diagram showing the activity of beta-galactosidase expressed on the surface of the outer membrane of *Bacillus subtilis* spores.
Figure 8:
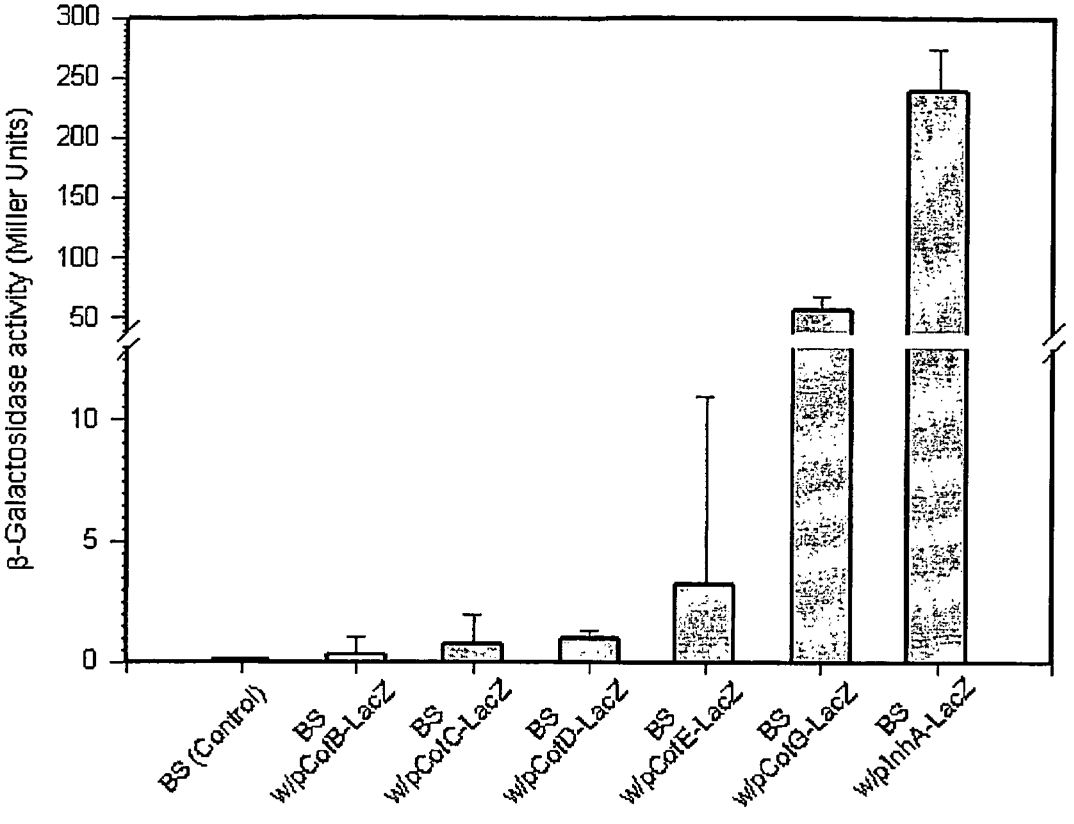
FIG. 8 is a graphic diagram showing the comparison between the activity of beta-galactosidase expressed on the surface of the outer membrane of *Bacillus subtilis* spores and that of the existing motifs for spore surface expression.
Figure 9:
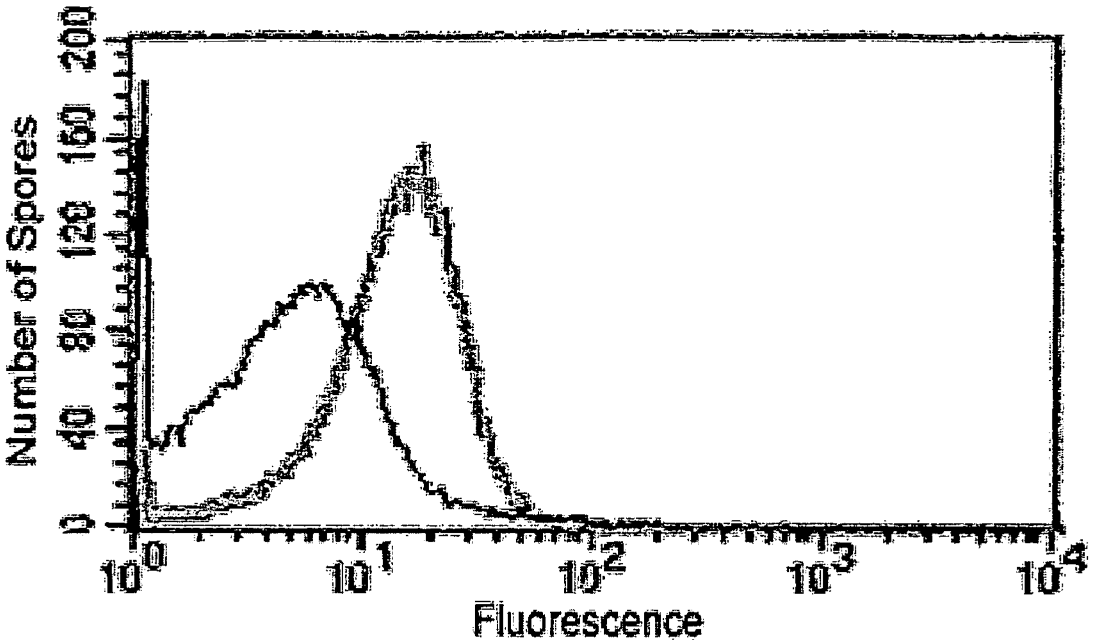
FIG. 9 is a graphic diagram showing the result of analysis using flow cytometer for the expression of beta-galactosidase on the surface of the outer membrane of *Bacillus subtilis* spores.

The separated spores were measured for beta-galactosidase activity by the method of Miller (Miller et al., *Experiments in Molecular Genetics*, Cold Spring Harbor Laboratory, NY, p. 352-5, 1972), and the results showed that the case where beta-galactosidase have been expressed on the surface of the spore outer membrane (BS w/InhA-lacZ) had a highly increased enzymatic activity compared to a control group (BS) (FIG. 7). Also, the enzymatic activity of the BS w/InhA-lacZ was compared with that of those known as motifs for spore surface expression, and as a result, it could be found that the BS w/InhA-lacZ showed a significantly higher activity than that of the existing spore surface expression technologies (FIG. 8). Meanwhile, the strains were analyzed with a flow cytometer (FACSCalibur, Becton Dickinson Co., USA) using an antibody specially binding to beta-galactosidase, and the results showed that beta-galactosidase was detected on the surface of the *Bacillus subtilis* spores transformed with pS-InhA-LacZ (FIG. 9).

Example 5

Expression of Green Fluorescent Protein on Surface of Spore Outer Membrane

Figure 10:
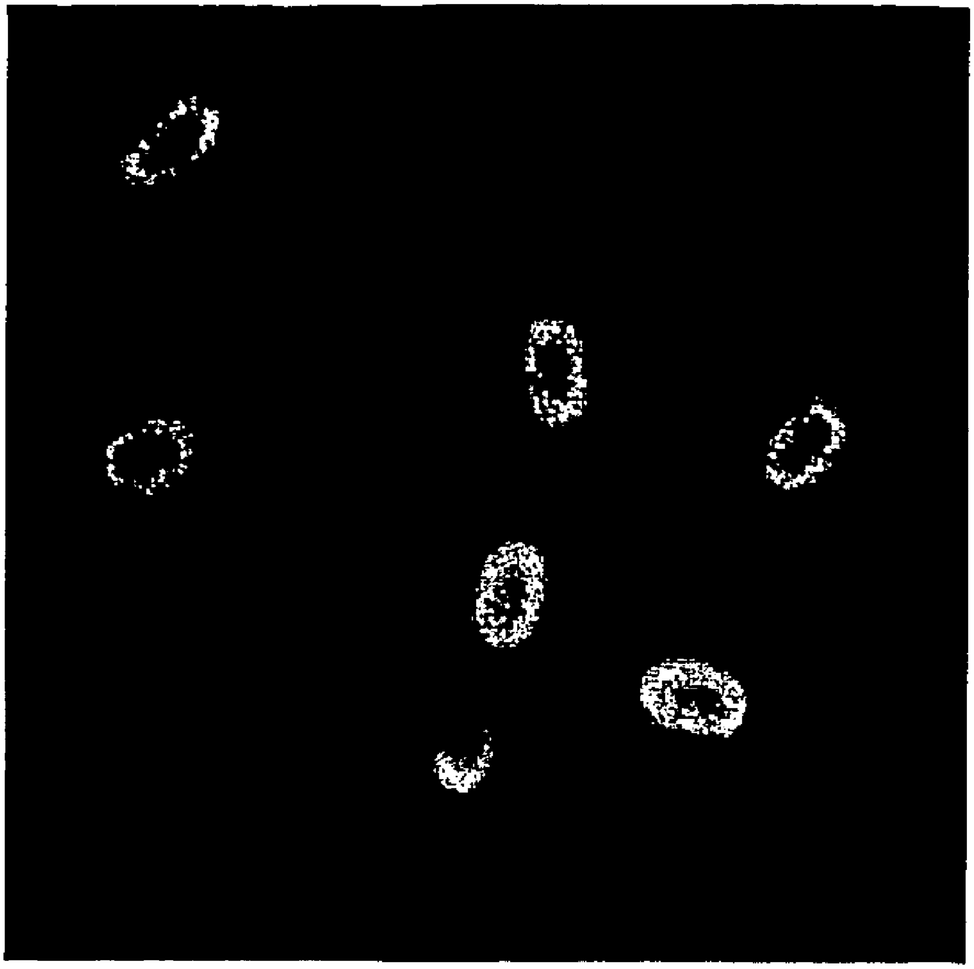
FIG. 10 is a photograph of surface-expressed EGFP taken by a confocal laser scanning microscope.

To express an enhanced green fluorescent protein (EGFP) on the surface of the spore outer membrane constituting the outermost portion of spores, the EGFP gene was inserted into the plasmid pS-InhA of Example 2. The resulting recombinant plasmid was introduced into *Bacillus subtilis* DB104 and cultured as in Example 3 to obtain spores. In order to examine if EGFP was expressed on the surface of the spore outer membrane, the surface-expressed EGFP was examined by CLSM (confocal laser scanning microscope; Carl Zeiss LSM 410, Germany). FIG. 10 is a photograph of EGFP taken by exposure to an argon laser with 488 nm wavelength. From this result, it could be found that EGFP was normally expressed on the spore surface.

Example 6

Patterning of Spores for Surface Expression

Figure 11:
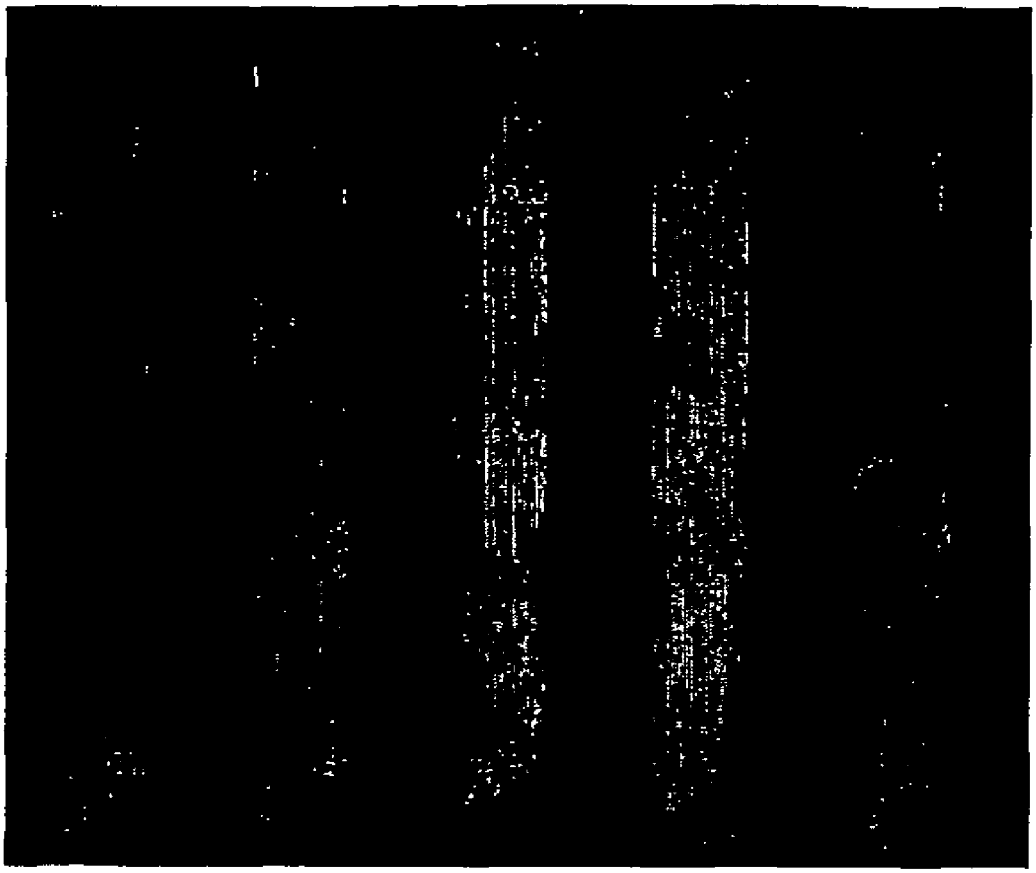
FIG. 11 shows a streptavidin-patterned substrate, which was obtained by the reaction of streptavidin on a slide glass on which biotin and poly(ethyleneglycol)amine has been patterned.

First, streptavidin was reacted on a slide glass on which biotin and poly(ethyleneglycol)amine (MW 5000) have been patterned. This gives a substrate on which streptavidin was patterned (FIG. 11).

Figure 12:
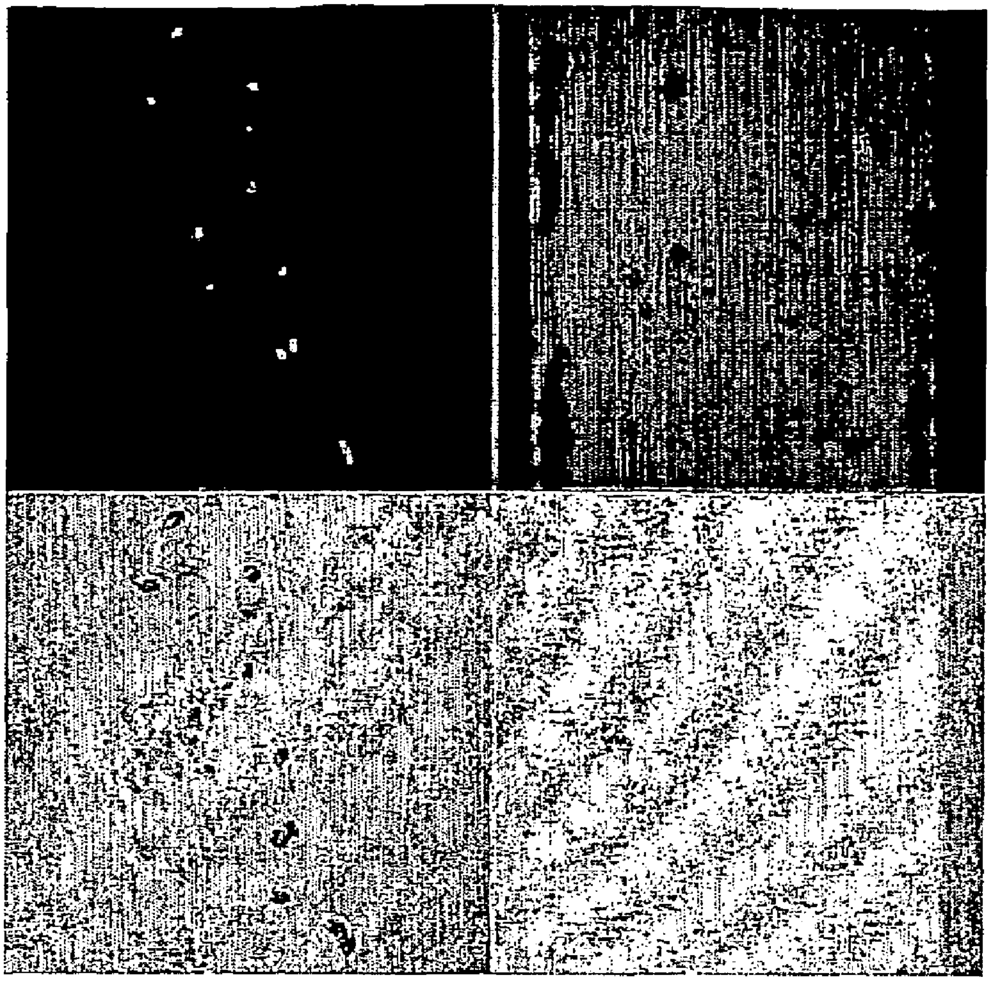
FIG. 12 shows that an antibody specifically binding to EGFP is reacted with spores having EGFP expressed on their surface, and the binding of the antibody to protein A is induced, and then, the bound substance is reacted on a streptavidin-patterned substrate to induce the patterning of spores.
Figure 13:
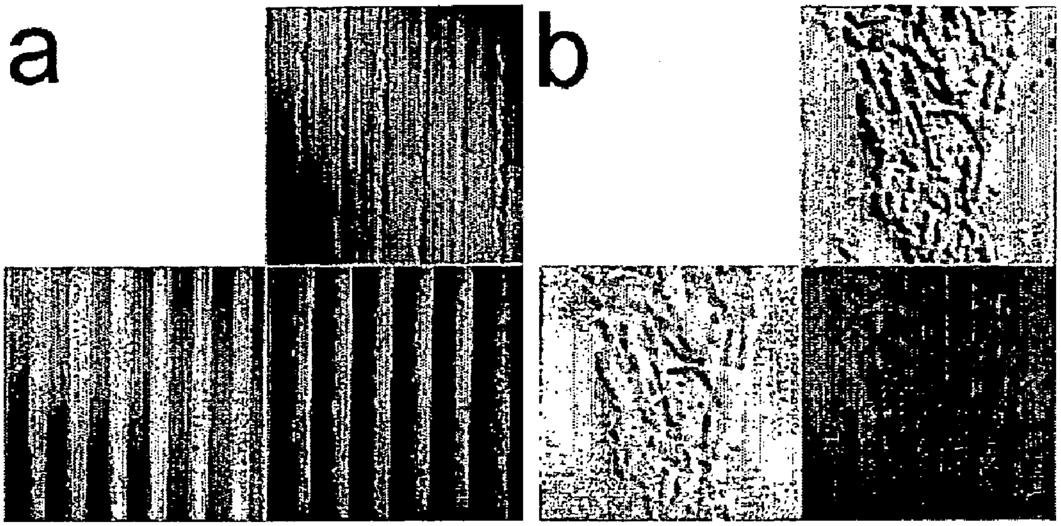
FIG. 13*a* shows that patterned spores are cultured in an LB agar medium so that they are grown into vegetative cells.
FIG. 13*b* is a photograph of the FIG. 13*a* which is magnified 12 times.

Meanwhile, the patterning of the cells and spores using EGFP, which have been surface-expressed in a fused form with the exosporium prepared in Example 5, was embodied. For this, an antibody specifically binding to EGFP was first reacted with the spores having the EGFP expressed on their surface, and then, the binding of the antibody to protein A was induced using a substance where the protein A is fused to biotin. Then, the resulting substance was reacted on the streptavidin-patterned substrate to induce the patterning of the spores (FIG. 12). The patterned spores were cultured in an LB agar medium for about 8-16 hours so that they were grown into vegetative cells (FIG. 13). This indicates that the patterning of live cells became possible. Thus, a protein array produced by the patterning method of the present invention can be used in a diagnostic kit using a protein chip, bioMEMS and a patterning method, gene expression analysis, the analysis of protein-protein, protein-ligand or antigen-antibody interaction, the analysis of metabolic processes, the screening of new or improved enzymes, combinatorial biochemical synthesis, and biosensors, etc.

Example 7

Figure 14:
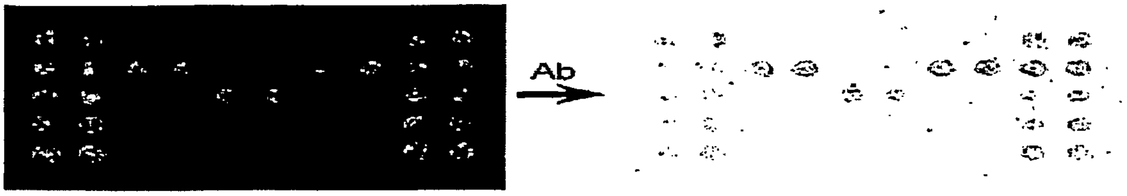
FIG. 14 is a photograph for protein arrays, which were obtained by expressing EGFP on the surface of the outer membrane of *Bacillus subtilis* spores and then immobilizing the resulting spores on an aldehyde slide.

Protein Array Using Gene Carriers Having Target Protein Expressed on their Surface $10^6$-$10^9$ gene carriers having EGFP expressed on their surface were attached to the surface of a slide glass (CEL Associates Co., USA) coated with an aldehyde functional group, by means of an automated arrayer. In this case, an amino group present on the protein of the gene carrier surface was reacted with the aldehyde group present on the slide glass surface to form a schiff-base, so that the gene carriers were covalently attached to the solid surface for protein arrays and protein chips. FIG. 14 is a fluorescent photograph for the protein arrayed EGFP and it after reaction with polyclonal antibody against GFP. Although the target protein expressed on the surface of the spore outer membrane was attached to the solid surface to lose its activity, it could be found that the target protein expressed on the spore outer membrane of the gene carriers has a constant direction. Accordingly, the protein array produced by the method of the present invention can be used in a diagnostic kit using a protein chip, bioMEMS and a patterning method, gene expression analysis, the analysis of protein-protein, protein-ligand or antigen-antibody interaction, the analysis of metabolic processes, the screening of new or improved enzymes, combinatorial biochemical synthesis, and biosensors, etc.

Predictive Example 1

Expression of Target Protein on Surface of Outer Membrane of *Bacillus cereus* Spores Strains very similar to *Bacillus cereus* include *Bacillus anthracis* and *Bacillus thuringiensis*, which all have a spore outer membrane at the outside of spores. In the case of *Bacillus anthracis*, bclA genes (SEQ ID NO: 11 to SEQ ID NO: 22) code for an exosporium that is glycoprotein forming a GXX collagen-like repeating region (Sylvestre, et al., *J. Bacteriol.,* 185:1555-63, 2003). In the case of *Bacillus cereus*, exsB, exsC, exsD, exsE, exsF, exsG, exsH, exsJ, and exsY genes (SEQ ID NO: 23 to SEQ ID NO: 31) encoding the exosporium (Todd, et al., *J. Bacteriol.,* 185:3373-8, 2003). Thus, such genes can be used as a matrix for surface expression.

The exosporium gene was amplified by PCR using the DNA of a *Bacillus anthracis* strain (KCTC 3561) as a template, and bclA1 primer (SEQ ID NO: 32) and bclA2 primer (SEQ ID NO: 33). The PCR product (exosporium gene) was cut with SalI and NheI, and inserted into the same site of the plasmid pSD1 produced in Example 1, to produce pS-bclA. If the gene of a target protein is inserted into the pS-bclA and then cells are transformed with the plasmid and cultured, the target protein can be expressed on the cell or spore surface. In addition to the bclA gene of the *Bacillus anthracis* (KCTC 3561), in the case of using the exsB, exsC, exsD, exsE, exsF, exsG, exsH, exsJ, and exsY genes of *Bacillus cereus* (KCTC 1092) as a matrix for surface expression, the target protein can be expressed on the cell or spore surface.

Predictive Example 2

Cell Surface Expression of CMCase Using Exosporium as Matrix

The exosporium, for which the bclA gene of *Bacillus anthracis* codes, has a collagen-like region with repeating amino acid sequences. Since an amino acid sequence of $(GPT)_5$GDTGTT type have repeating regions of one to eight depending on the kind of a host cell, at the middle position of the exosporium (Sylvestre et al., *Mol. Microbiol.,* 45:169-78, 2002; *J. Bacteriol.,* 185:1555-63, 2003), it can be used in the expression of a target protein on the surface of the outer membrane of genus *Bacillus* spores, and also in the expression on the cell surface of gram-positive bacteria and gram-negative bacteria.

Predictive Example 3

Antibody Production Method Using Gene Carriers Having Target Protein Expressed on their Surface If an antigen capable of inducing an immune response in vivo was expressed on the surface of gene carriers, antibody production can be induced using the gene carriers. For this, a gene encoding the antigen is inserted into a plasmid which can be replicated in host cells in a form capable of expression. The host cells are transformed with the plasmid. The transformed host cells are cultured in a suitable medium so that the antigen is expressed on the surface of the spore outer membrane of the gene carriers. The gene carriers having the antigen expressed on their surface is suspended in a buffer, and added with the same volume of Freund's complete adjuvant. After the mixed solution is stirred to be oil suspension, it is administered intravenously to a 6 to 8-week old BALB/c mouse. At 3-4 weeks after the administration, it is administered again. Next, booster administration is performed two or three times to induce antibody production.

Predictive Example 4

Method of Separating Certain Substance from Mixture Using Gene Carriers Having Target Protein Expressed on their Surface Using gene carriers having a binding domain expressed on their surface, a certain substance can be separated from a mixture. For this, error-prone PCR is first performed on a gene encoding the binding domain, in which the target protein gene is amplified using a plasmid or chromosome containing the target protein gene as a template, and a primer specifically binding to the target protein gene. Then, the PCR product is inserted into a plasmid which can be replicated in each host in a form capable of expression. Then, a library is established in host cells. The host cells are transformed with the vector library for surface expression, and the binding domain mutant is expressed in the host cells to obtain a gene carrier library expressed on the gene carrier surface. Then, the gene carriers where the binding domain mutant having the desired characteristics was expressed on the spore outer membrane are screened. The screened gene carriers are separated and multiplied, to produce gene carriers having the binding domain expressed on the spore outer membrane. Then, the gene carriers having the binding domain expressed on the spore outer membrane is contacted with a mixture to separate a certain substance.

INDUSTRIAL APPLICABILITY

As described above, the present invention provides the method for the surface expression of a target protein on gene carrier, in which the target protein is expressed in a fused form with the exosporium of gene carriers, and also provides the method for the production of a protein array. Furthermore, the present invention provides the method for inducing an immune response to an antigen in Vertebrata, the method for separating a certain substance from a mixture, and the method for improving the target protein. Moreover, the present invention provides the vector for expressing the target protein on the surface of the spore outer membrane of gene carriers, as well as the recombinant microorganism transformed with the expression vector. The method for expressing the target protein on the surface of the spore outer membrane of the gene carriers has effects in that a variety of the target proteins can be expressed and the level of surface expression of the target protein is increased compared to the existing technology, and also the structural stability of the gene carriers having the target protein expressed on their surface, the viability of the host, and the rapidity of the screening method, are greatly increased.

What is claimed is:

1. A surface expression vector for use in a spore or cell, the vector comprising:

a replication origin;

an antibiotic-resistant gene;

a restriction enzyme site;

a gene encoding a protein of the exosporium selected from the group consisting of inhA isolated from *Bacillus thuringiensis*, bclA isolated from *Bacillus anthracis*, exsB, exsC, exsD, exsE, exsF, exsG, exsH, exsJ and exsY isolated from *Bacillus cereus*; and a gene encoding a target protein, wherein expression of the vector in the spore or cell results in expression of a fusion protein on the spore or cell surface, wherein the fusion protein comprises the exosporium protein and the target protein.

2. A recombinant bacterium which is obtained by transforming a bacterium selected from the group consisting of gram-negative bacteria and gram-positive bacteria with the expression vector of claim 1.

* * * * *

UNITED STATES PATENT AND TRADEMARK OFFICE

CERTIFICATE OF CORRECTION

PATENT NO. : 8,030,064 B2
APPLICATION NO. : 10/572224
DATED : October 4, 2011
INVENTOR(S) : Sang Yup Lee It is certified that error appears in the above-identified patent and that said Letters Patent is hereby corrected as shown below:

Cover page Item 56 under "References Cited" line 6 "Other Publications" the Georgiou reference title "Analysis of large libraried..." should be -- Analysis of large libraries...--.

Signed and Sealed this
Twenty-fourth Day of April, 2012

David J. Kappos
*Director of the United States Patent and Trademark Office*